US010059960B2

(12) United States Patent
Sampson et al.

(10) Patent No.: US 10,059,960 B2
(45) Date of Patent: Aug. 28, 2018

(54) AXMI221Z, AXMI222Z, AXMI223Z, AXMI224Z, AND AXMI225Z DELTA-ENDOTOXIN GENES AND METHODS FOR THEIR USE

(71) Applicant: Athenix Corp., Morrisville, NC (US)

(72) Inventors: Kimberly Sampson, Durham, NC (US); Daniel Tomso, Bahama, NC (US)

(73) Assignee: Athenix Corp., Morrisville, NC (US)

( * ) Notice: Subject to any disclaimer, the term of this patent is extended or adjusted under 35 U.S.C. 154(b) by 99 days.

(21) Appl. No.: 14/932,494

(22) Filed: Nov. 4, 2015

(65) Prior Publication Data

US 2016/0053278 A1 Feb. 25, 2016

Related U.S. Application Data

(62) Division of application No. 14/207,950, filed on Mar. 13, 2014, now Pat. No. 9,206,249, which is a division of application No. 13/030,415, filed on Feb. 18, 2011, now Pat. No. 8,686,124.

(60) Provisional application No. 61/305,802, filed on Feb. 18, 2010.

(51) Int. Cl.
*C12N 15/82* (2006.01)
*C07K 14/325* (2006.01)
*A01N 37/46* (2006.01)
*A01N 63/02* (2006.01)
*C07K 16/12* (2006.01)

(52) U.S. Cl.
CPC ......... *C12N 15/8286* (2013.01); *A01N 37/46* (2013.01); *A01N 63/02* (2013.01); *C07K 14/325* (2013.01); *C07K 16/1278* (2013.01); *C12N 15/8279* (2013.01)

(58) Field of Classification Search
None
See application file for complete search history.

(56) References Cited

U.S. PATENT DOCUMENTS

| | | | |
|---|---|---|---|
| 5,530,195 A | 6/1996 | Kramer | |
| 5,558,071 A | 9/1996 | Ward et al. | |
| 6,204,246 B1 * | 3/2001 | Bosch | A01N 63/02 514/21.2 |
| 7,169,971 B2 | 1/2007 | Arnaut et al. | |
| 7,253,343 B2 | 8/2007 | Carozzi et al. | |
| 8,461,129 B2 | 6/2013 | Bolduc et al. | |
| 2004/0016020 A1 | 1/2004 | Arnaut | |
| 2005/0138685 A1 | 6/2005 | Flannagan et al. | |
| 2011/0028412 A1 | 2/2011 | Cappello et al. | |
| 2013/0041004 A1 | 2/2013 | Drager et al. | |
| 2013/0096073 A1 | 4/2013 | Sidelman | |

OTHER PUBLICATIONS

Argolo-Filho et al, Insects (2014) 5:62-91.*
Pardo Lopez et al, Peptides (2009) 30:589-595.*
Aronson et al, FEMS Microbiol. Lett. (2001) 195:1-8.*
Herrero et al., Biochem. J. (2004) 384:507-513.*
Abdul-Rauf et al, Curr. Microbiol. (1999) 39:94-98.*
Invitation to Pay Additional Fees and Partial Search Report issued in PCT/US2011/025172, dated Aug. 19, 2011.
Wang, J. H. et al., "Bacillus thuringiensis insecticidal crystal protein gene", unpublished, Accession AA039720, Dec. 1, 2005.
Stobdan, T. et al., "Cloning and nucleotide sequence of a novel cry gene from Bacillus thuringiensis", Biotechnol. Lett., vol. 26, No. 14, p. 1153-1156, 2004, Accession AAQ88259.
Zhang, Q. et al., "Cloning of cry2Ah2 gene from Bacillus thuringiensis", unpublished, Accession ACL80665, Jan. 19, 2009.
Smulevitch, S. V. et al., "Nucleotide sequence of a novel delta-endotoxin gene crylg of *Bacillus thuringiensis* ssp. *galleriae*", FEBS Lett. 293 (1-2), 25-28, 1991, Accession Q99031.
Aronson et al. 2001. Why Bacillus Thuringiensis insecticidal toxins are so effective: unique features of their mode of action. FEMS Microbiol Lett. 195:1-8.
de Maagd et al. 1999. Identification of Bacillus thuringiensis delta-endotoxin Cry1C domain III amino acid residues involved in insect specificity. Appl Environ Microbiol. 65:4369-4374.
de Maagd et al. 2001. How Bacillus thuringiensis has evolved specific toxins to colonize the insect world. Trends Genetics. 17(4):193-199.
Guo et al. 2004. Protein tolerance to random amino acid change. PNAS. 101:9205-9210.
Tounsi et al. 2003. Cloning and study of the expression of a novel Cry1 la-type gene from *Bacillus thuringiensis* subsp. *kurstaki*, J. Appl Microbiol. 95:23-28.
Canadian Bt Toxin Specificity Database. Accessed Nov. 26, 2012. http://cfs.nrcan.gc.ca/projects/119/2.
Yao, J. et al., submitted May 31, 2002 to Biotechnology, Institute of Plant Protection, CAAS, 2 Yuan Ming Yuan Xi Lu, Haidian District, Beijing. China, Accession AAQ08233.
Saraswathi et al, Elec. J. Biotechnol. (2004) 7:180-190.
Pardo Lopez et al, Strategies to Improve the Insecticidal Activity of Cry Toxins from Bacillus thuringiensis, Peptides (2009) 30:589-595.
Herrero et al, Mutations in the Bacillus thuringiensis Cry1Ca Toxin Demonstrate the Role of Domains II and III in Specificity Towards Spodoptera exigua Larvae, Biochem. J. (2004) 384:507-513.

(Continued)

*Primary Examiner* — Mykola V Kovalenko

(57) ABSTRACT

Compositions and methods for conferring lepidoptericidal activity to bacteria, plants, plant cells, tissues and seeds are provided. Compositions comprising a coding sequence for the Axmi222z toxin polypeptide are provided. The Axmi222z coding sequences can be used in DNA constructs or expression cassettes for transformation and expression in plants and bacteria. Compositions also comprise transformed bacteria, plants, plant cells, tissues, and seeds. In particular, isolated Axmi222z toxin nucleic acid molecules are provided. Additionally, amino acid sequences corresponding to the Axmi222z polynucleotides are encompassed, and antibodies specifically binding to those amino acid sequences. In particular, the present invention provides for isolated nucleic acid molecules comprising nucleotide sequences encoding the amino acid sequence shown in SEQ ID NO:24-26, or the nucleotide sequence set forth in SEQ ID NO:2, 7, 12, and 17, as well as variants and fragments thereof.

23 Claims, No Drawings

Specification includes a Sequence Listing.

(56) References Cited

OTHER PUBLICATIONS

Abdul-Rauf et al, Mutations of Loop 2 and Loop 3 Residues in Domain II of Bacillus thuringiensis CrylC delta-Endotoxin Affect Insecticidal Specificity and Inidial Binding to Spodoptera littoralis and Aedes aegypti Midgut Membranes, Curr. Microbial. (1999) 39:94-98.

Argolo-Filho et al, Bacillus thuringiensis Is an Environmental Pathogen and Host-Specificity Has Developed as an Adaptation to Human-Generated Ecological Niches, Insects (2014) 5:62-91.

* cited by examiner

AXMI221Z, AXMI222Z, AXMI223Z, AXMI224Z, AND AXMI225Z DELTA-ENDOTOXIN GENES AND METHODS FOR THEIR USE

CROSS REFERENCE TO RELATED APPLICATION

This application is a divisional of U.S. patent application Ser. No. 14/207,950, filed Mar. 13, 2014, which is a divisional of U.S. patent application Ser. No. 13/030,415, filed Feb. 18, 2011, now U.S. Pat. No. 8,686,124, issued on Apr. 1, 2014, which claims the benefit of U.S. Provisional Application Ser. No. 61/305,802, filed Feb. 18, 2010, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "APA069US01DDSEQLIST.txt", created on Nov. 4, 2015, and having a size of 132 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Hemipteran, Dipteran, and Coleopteran larvae. These proteins also have shown activity against *Hymenoptera, Homoptera, Phthiraptera, Mallophaga*, and *Acari* pest orders, as well as other invertebrate orders such as *Nemathelminthes, Platyhelminthes*, and *Sarcomastigorphora* (Feitelson (1993) The *Bacillus Thuringiensis* family tree. In *Advanced Engineered Pesticides*, Marcel Dekker, Inc., New York, N.Y.) These proteins were originally classified as CryI to CryV based primarily on their insecticidal activity. The major classes were *Lepidoptera*-specific (I), *Lepidoptera*- and *Diptera*-specific (II), *Coleoptera*-specific (III), *Diptera*-specific (IV), and nematode-specific (V) and (VI). The proteins were further classified into subfamilies; more highly related proteins within each family were assigned divisional letters such as CryIA, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Because of the devastation that insects can confer, and the improvement in yield by controlling insect pests, there is a continual need to discover new forms of pesticidal toxins.

SUMMARY OF INVENTION

Compositions and methods for conferring pesticidal activity to bacteria, plants, plant cells, tissues and seeds are provided. Compositions include nucleic acid molecules encoding sequences for pesticidal and insectidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules are provided that encode a pesticidal protein. Additionally, amino acid sequences corresponding to the pesticidal protein are encompassed. In particular, the present invention provides for an isolated nucleic acid molecule comprising a nucleotide sequence encoding the amino acid sequence shown in SEQ ID NO:21-32 or a nucleotide sequence set forth in SEQ ID NO:1-5, as well as variants and fragments thereof. Nucleotide sequences that are complementary to a nucleotide sequence of the invention, or that hybridize to a sequence of the invention are also encompassed. Synthetic nucleotide sequences encoding the polypeptides disclosed herein are also set forth in SEQ ID NO:6-20.

Methods are provided for producing the polypeptides of the invention, and for using those polypeptides for controlling or killing a lepidopteran, hemipteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

DETAILED DESCRIPTION

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of *Bacillus* or other species. The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling, for example, with members of the Cry1, Cry2, and Cry9 families of endotoxins. The proteins find use in controlling or killing lepidopteran, hemipteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the *Lepidoptera*, *Diptera*, and *Coleoptera* orders, or the *Nematoda* phylum, or a protein that has homology to such a protein. Pesticidal proteins have been isolated from organisms including, for example, *Bacillus* sp., *Clostridium bifermentans* and *Paenibacillus popilliae*. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Pesticidal proteins encompass delta-endotoxins. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), Microbiol. Mol. Biol. Rev. 62:807-813, and for regular updates see Crickmore et al. (2003) "*Bacillus thuringiensis* toxin nomenclature," on the worldwide web at biols.susx.ac.uk/Home/Neil_Crickmore/Bt/index.

Thus, provided herein are novel isolated nucleotide sequences that confer pesticidal activity. These isolated nucleotide sequences encode polypeptides with homology to known delta-endotoxins or binary toxins. Also provided are the amino acid sequences of the pesticidal proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "recombinant" nucleic acid sequence (or DNA) is used herein to refer to a nucleic acid sequence (or DNA) that is no longer in its natural environment, for example in an in vitro or in a recombinant bacterial or plant host cell. In some embodiments, an isolated or recombinant nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various embodiments, a delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:1-20, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the pesticidal protein encoded by this nucleotide sequence are set forth in SEQ ID NO:21-32.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. By "retains activity" is intended that the fragment will have at least about 30%, at least about 50%, at least about 70%, 80%, 90%, 95% or higher of the pesticidal activity of the pesticidal protein. In one embodiment, the pesticidal activity is coleoptericidal activity. In another embodiment, the pesticidal activity is lepidoptericidal activity. In another embodiment, the pesticidal activity is nematocidal activity. In another embodiment, the pesticidal activity is diptericidal activity. In another embodiment, the pesticidal activity is hemiptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450 contiguous amino acids, or up to the total number of amino acids present in a full-length pesticidal protein of the invention. In some embodiments, the fragment is a proteolytic cleavage fragment. For example, the proteolytic cleavage fragment may have an N-terminal or a C-terminal truncation of at least about 100 amino acids, about 120, about 130, about 140, about 150, or about 160 amino acids relative to SEQ ID NO:21-32. In some embodiments, the fragments encompassed herein result from the removal of the C-terminal crystallization domain, e.g., by proteolysis or by insertion of a stop codon in the coding sequence. See, for example, the truncated amino acid sequences set forth in SEQ ID NO:22, 23, 25, 26, and 32. It will be understood that the truncation site may vary by 1, 2, 3, 4, 5, 6, 7, 8, 9, 10, 11, 12, 13, 14, 15, or more amino acids on either side of the truncation site represented by the terminus of SEQ ID NO:22, 23, 25, 26, and 32 (compared to the corresponding full-length sequence).

Preferred pesticidal proteins of the present invention are encoded by a nucleotide sequence sufficiently identical to the nucleotide sequence of SEQ ID NO:1-20. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., the sequence disclosed herein as any of SEQ ID NO:1-20). The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) J. Mol. Biol. 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10. The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal protein sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, New York).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m = 81.5°$ C. $+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, New York).

Isolated Proteins and Variants and Fragments Thereof

Pesticidal proteins are also encompassed within the present invention. By "pesticidal protein" is intended a protein having the amino acid sequence set forth in SEQ ID NO:21-32. Fragments, biologically active portions, and variants thereof are also provided, and may be used to practice the methods of the present invention. An "isolated protein" is used to refer to a protein that is no longer in its natural environment, for example in vitro or in a recombinant bacterial or plant host cell. An "isolated protein" or a "recombinant protein" is used to refer to a protein that is no longer in its natural environment, for example in vitro or in a recombinant bacterial or plant host cell.

"Fragments" or "biologically active portions" include polypeptide fragments comprising amino acid sequences sufficiently identical to the amino acid sequence set forth in SEQ ID NO:21-32, and that exhibit pesticidal activity. A biologically active portion of a pesticidal protein can be a polypeptide that is, for example, 10, 25, 50, 100, 150, 200, 250 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:21-32. The invention encompasses other fragments, however, such as any fragment in the protein greater than about 10, 20, 30, 50, 100, 150, 200, 250, or 300 amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:21-32. Variants also include polypeptides encoded by a nucleic acid molecule that hybridizes to the nucleic acid molecule of SEQ ID NO:1-20, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity relative to the native protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. See, for example, the alternate start site for the AXMI223z protein set forth in SEQ ID NO: 28 and the alternate start site for AXMI224z protein set forth in SEQ ID NO:30. These pesticidal proteins are encompassed in the present invention and may be used in the methods of the present invention. It will be understood that, when expressed in plants, it will be necessary to alter the alternate start codon to ATG for proper translation.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of SEQ ID NO:21-32, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the pesticidal protein mutations in a non-mutagenic strain, and identify mutated genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391;

Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A pesticidal sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol.*

Biol. Rep. 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the novel toxin sequences disclosed herein. In various embodiments, the transgenic plant further comprises one or more additional genes for insect resistance (e.g., Cry1, such as members of the Cry1A, Cry1B, Cry1C, Cry1D, Cry1E, and Cry1F families; Cry2, such as members of the Cry2A family; Cry9, such as members of the Cry9A, Cry9B, Cry9C, Cry9D, Cry9E, and Cry9F families; etc.). It will be understood by one of skill in the art that the transgenic plant may comprise any gene imparting an agronomic trait of interest.

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

Use in Pesticidal Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, hemipteran, dipteran, or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides:

Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethonmethyl, Pirimicarb, Methiocarb; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides:
Carbofuran, Organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

The following examples are offered by way of illustration and not by way of limitation.

EXPERIMENTAL EXAMPLES

Example 1. Discovery of Novel Pesticidal Genes from *Bacillus thuringiensis*

Novel pesticidal genes were identified from bacterial strain Zj22 using the following steps:
Preparation of extrachromosomal DNA from the strain. Extrachromosomal DNA contains a mixture of some or all of the following: plasmids of various size; phage chromosomes; genomic DNA fragments not separated by the purification protocol; other uncharacterized extrachromosomal molecules.
Mechanical or enzymatic shearing of the extrachromosomal DNA to generate size-distributed fragments.
Sequencing of the fragmented DNA by high-throughput pyrosequencing methods.
Identification of putative toxin genes via homology and/or other computational analyses.
When required, sequence finishing of the gene of interest by one of several PCR or cloning strategies (e.g. TAIL-PCR).

TABLE 1

Novel genes identified from strain Zj22

| Gene name | Molecular weight (kD) | Closest homolog | Nucleotide SEQ ID NO | Amino acid SEQ ID NO |
|---|---|---|---|---|
| Axmi221z | 138.3 | 62.1% Cry9Aa<br>60.1% Cry1Aa<br>84.0% Cry9Aa (truncated) | 1 | 21<br>22<br>(truncated)<br>23<br>(truncated) |
| Axmi222z | 141.1 | 86.5% Cry1Bf<br>86.4% Cry1Ba<br>76.2% Cry1Bf (truncated)<br>76.2% Cry1Ba (truncated) | 2 | 24<br>25<br>(truncated)<br>26<br>(truncated) |
| Axmi223z | 80.9 | 84.7% Cry1Ia<br>82.1% Cry1If<br>81.9% Cry1Id<br>81.8% Cry1Ie<br>81.2% Cry1Ib<br>78.2% Cry1Ic | 3 | 27<br>28<br>(alternate start site) |
| Axmi224z | 75 | 98.9% Cry2Af<br>93.5% Cry2Ab1<br>93.0% Cry2Ae1<br>91.2% Cry2Ad1 | 4 | 29<br>30<br>(alternate start site) |
| Axmi225z | 133.2 | 98.6% Cry1Ab18<br>94.8% Axmi112<br>94.8% Cry1Ae1<br>94.8% Cry1Ab1<br>98.6% Cry1Ab18 (truncated)<br>98.0% Cry1Ab1 (truncated)<br>95.6% Cry1Ae1 (truncated)<br>95.4% Axmi112 (truncated) | 5 | 31<br>32<br>(truncated) |

The toxin gene disclosed herein is amplified by PCR from pAX980, and the PCR product is cloned into the *Bacillus* expression vector pAX916, or another suitable vector, by methods well known in the art. The resulting *Bacillus* strain, containing the vector with axmi gene is cultured on a conventional growth media, such as CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation is evident by microscopic examination. Samples are prepared and tested for activity in bioassays.

Example 2. Assays for Pesticidal Activity

The nucleotide sequences of the invention can be tested for their ability to produce pesticidal proteins. The ability of a pesticidal protein to act as a pesticide upon a pest is often assessed in a number of ways. One way well known in the art is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests* and *Journal of Economic Entomology* or by discussion with members of the Entomological Society of America (ESA).

In some embodiments, the DNA regions encoding the toxin domains of delta-endotoxins disclosed herein are cloned into the *E. coli* expression vector pMAL-C4x behind the malE gene coding for Maltose binding protein (MBP). These in-frame fusions result in MBP-Axmi fusion proteins expression in *E. coli*.

For expression in *E. coli*, BL21*DE3 are transformed with individual plasmids. Single colonies are inoculated in LB supplemented with carbenicillin and glucose, and grown overnight at 37° C. The following day, fresh medium is inoculated with 1% of overnight culture and grown at 37° C. to logarithmic phase. Subsequently, cultures are induced with 0.3 mM IPTG overnight at 20° C. Each cell pellet is suspended in 20 mM Tris-Cl buffer, pH 7.4+200 mM NaCl+1 mM DTT+protease inhibitors and sonicated. Analysis by SDS-PAGE can be used to confirm expression of the fusion proteins.

Total cell free extracts are then run over amylose column attached to fast protein liquid chromatography (FPLC) for affinity purification of MBP-axmi fusion proteins. Bound fusion proteins are eluted from the resin with 10 mM maltose solution. Purified fusion proteins are then cleaved with either Factor Xa or trypsin to remove the amino terminal MBP tag from the Axmi protein. Cleavage and solubility of the proteins can be determined by SDS-PAGE

Example 3. Expression and Purification of Axmiz Genes

Truncated versions of axmi221z and axmi222z were cloned into the maltose-binding protein (MBP) expression vector, resulting in pAX5092 and pAX5093, respectively. Expression of the resulting fusion protein was induced by IPTG. Protein was then purified through a maltose column and cleaved with protease Factor Xa to generate the untagged, purified protein. The truncated 6-his axmi221z and axmi222z proteins were also purified on a cobalt column and submitted for bioassays.

Full-length and truncated versions of some genes were cloned into vector pRSF-1b as shown in Table 2. By virtue of cloning into this vector, the resulting expressed protein contains an additional six N-terminal histidine residues.

The DNA regions encoding the toxin domains of some genes were separately cloned into an *E. coli* expression vector pMAL-C4x behind the malE gene coding for Maltose binding protein (MBP) as shown in Table 2. These in-frame fusions resulted in MBP-AXMI fusion proteins expression in *E. coli*. Each of the proteins produced from the constructs above were tested in bioassays as a 10× concentrated pellet.

TABLE 2

Axmiz constructs

| gene | construct name | backbone vector | SEQ ID NO: of protein encoded by construct |
|---|---|---|---|
| Axmi221z (full length) | pAX5095 | pRSF-1b | 21 |
| Axmi221z (full length) | pAX7611 | pAX916 | 21 |
| Axmi221z (trun2) | pAX5092 | pMAL-C4x | 23 |
| Axmi221z (trun2) | pAX5094 | pRSF-1b | 23 |
| Axmi221z (trun2) | pAX7610 | pRSF-1b | 23 |
| Axmi222z (full length) | pAX5097 | pRSF-1b | 24 |
| Axmi222z (full length) | pAX7613 | pAX916 | 24 |
| Axmi222z (trun2) | pAX5093 | pMAL-C4x | 26 |
| Axmi222z (trun2) | pAX5096 | pRSF-1b | 26 |
| Axmi222z (trun2) | pAX7612 | pAX916 | 26 |
| Axmi223z (full length) | pAX6887 | pMAL-C4x | 27 |
| Axmi223z (alternate start site) | pAX6888 | pMAL-C4x | 28 |
| Axmi224z (alternate start site) | pAX7634 | pRSF-1b | 30 |
| Axmi224z (alternate start site) | pAX6890 | pMAL-C4x | 30 |
| Axmi225z (trun) | pAX6891 | pMAL-C4x | 32 |

For expression of protein in *E. coli*, BL21*DE3 was transformed with individual plasmids. A single colony was inoculated into LB media supplemented with carbenicillin and glucose, and grown overnight at 37° C. The following day, fresh medium was inoculated with 1% of overnight culture and grown at 37° C. to logarithmic phase. Subsequently, cultures were induced with 0.3 mM IPTG overnight at 20° C. Each cell pellet was suspended in 20 mM Tris-Cl buffer, pH 7.4+200 mM NaCl+1 mM DTT+protease inhibitors and sonicated. Analysis by SDS-PAGE confirmed expression of fusion proteins.

Total cell free extracts were loaded onto an FPLC equipped with an amylose column, and the MBP-AXMI fusion proteins were purified by affinity chromatography. Bound fusion protein was eluted from the resin with 10 mM maltose solution. Purified fusion proteins were then cleaved with either Factor Xa or trypsin to remove the amino terminal MBP tag from the AXMIz protein. Cleavage and solubility of the proteins was determined by SDS-PAGE.

Example 4. Activity of Proteins Expressed from Axmiz Genes in Bioassays

Bioassay of the expressed Axmiz genes resulted in observance of the following activities on insect pests:

TABLE 3

Activity of Expressed Proteins in Bioassay

| Plasmids | Gene | BCW | CPB | DBM | ECB | FAW |
|---|---|---|---|---|---|---|
| pAX5095 | Axmi221z full length | | | | | Slight Stunt, No Mortality |
| pAX7611 | Axmi221z full length | | | Severe stunt, >75% Mortality | | |
| pAX5092 | Axmi221z trun2 | | | Severe stunt, >75% Mortality | Severe stunt, >75% Mortality | |
| pAX5094 | Axmi221z trun2 | | Stunt | | Slight Stunt, No Mortality | |
| pAX7610 | Axmi221z trun2 | | | Severe stunt, >75% Mortality | | |
| pAX5097 | Axmi222z full length | | | | | |
| pAX7613 | Axmi222z full length | Slight Stunt, No Mortality | | Severe stunt, >75% Mortality | Severe stunt, >75% Mortality | |
| pAX5093 | Axmi222z trun2 | | | | | |
| pAX5096 | Axmi222z trun2 | | | | | |
| pAX7612 | Axmi222z trun2 | | | Severe stunt, >75% Mortality | Severe stunt, >75% Mortality | Stunt, No Mortality |
| pAX6887 | axmi223z full length | Stunt, No Mortality | Severe stunt | Severe stunt, >75% Mortality | Severe stunt, >75% Mortality | Stunt, No Mortality |
| pAX6888 | axmi223z alt start | Stunt, No Mortality | Severe stunt | Severe stunt, >75% Mortality | Severe stunt, >75% Mortality | Stunt, No Mortality |
| pAX7634 | Axmi224z alt start | | | | Severe stunt, >75% Mortality | Strong Stunt, No Mortality |
| pAX6890 | axmi224z alt start | Slight Stunt, <<5No Mortality % Mortality5% Mortality | | Severe stunt, >75% Mortality | Severe stunt, >75% Mortality | Stunt, No Mortality |
| pAX6891 | axmi225z trun | Slight Stunt, No Mortality | | Severe stunt, >75% Mortality | Severe stunt, >75% Mortality | Stunt, No Mortality |

TABLE 4

Activity of Expressed Proteins in Bioassay

| Plasmid | Gene | Hv | Hz | SCB | SWCB | VBC |
|---|---|---|---|---|---|---|
| pAX5095 | Axmi221z full length | | | | Severe stunt, >75% Mortality | Severe stunt, <25% Mortality |
| pAX7611 | Axmi221z full length | Strong Stunt, No Mortality | | Strong Stunt, <25% Mortality | | |
| pAX5092 | Axmi221z trun2 | Strong Stunt, <25% Mortality | | Severe stunt, >75% Mortality | Severe stunt, >75% Mortality | Severe stunt, >75% Mortality |
| pAX5094 | Axmi221z trun2 | Strong Stunt, No Mortality | | | Severe stunt, >75% Mortality | Severe stunt, <25% Mortality |
| pAX7610 | Axmi221z trun2 | | | Strong Stunt, <25% Mortality | | |
| pAX5097 | Axmi222z full length | | | | Severe stunt, >75% Mortality | |

TABLE 4-continued

Activity of Expressed Proteins in Bioassay

| Plasmid | Gene | Hv | Hz | SCB | SWCB | VBC |
|---|---|---|---|---|---|---|
| pAX7613 | Axmi222z full length | Severe stunt, >75% Mortality | | Severe stunt, >75% Mortality | | Severe stunt, >75% Mortality |
| pAX5093 | Axmi222z trun2 | Severe stunt, >75% Mortality | | Severe stunt, >75% Mortality | Severe stunt, >75% Mortality | Severe stunt, >75% Mortality |
| pAX5096 | Axmi222z trun2 | Severe stunt, >75% Mortality | | | | Severe stunt, >75% Mortality |
| pAX7612 | Axmi222z trun2 | | | Severe stunt, >75% Mortality | Severe stunt, >75% Mortality | |
| pAX6887 | axmi223z full length | Stunt, No Mortality | Stunt, No Mortality | Severe stunt, >75% Mortality | Severe stunt, >75% Mortality | Strong Stunt, No Mortality |
| pAX6888 | axmi223z alt start | Severe stunt, <25% Mortality | Strong Stunt, <75% Mortality | Severe stunt, >75% Mortality | Severe stunt, >75% Mortality | Strong Stunt, No Mortality |
| pAX7634 | Axmi224 alt start | Severe stunt, >75% Mortality | Severe stunt, >75% Mortality | Severe stunt, <25% Mortality | Strong Stunt, No Mortality | Severe stunt, >75% Mortality |
| pAX6890 | axmi224z alt start | Severe stunt, >75% Mortality | Severe stunt, >75% Mortality | Severe stunt, >75% Mortality | Severe stunt, No Mortality | Severe stunt, >75% Mortality |
| pAX6891 | axmi225z trun | Severe stunt, >75% Mortality | Severe stunt, >75% Mortality | Severe stunt, >75% Mortality | Severe stunt, >75% Mortality | Severe stunt, >75% Mortality |

BCW: Black cutworm
CPB: Colorado Potato Beetle
DBM: Diamond Back Moth
ECB: European Cornborer
FAW: Fall armyworm
Hv: *Helitothis virescens*
Hz: *Heliothis zea*
SCB: Southern cornborer SWCB: Southwestern Cornborer VBC: Velvet Bean Caterpillar

Example 5. Vectoring of Genes for Plant Expression

The coding regions of the invention are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

In one aspect of the invention, synthetic DNA sequences are designed and generated. These synthetic sequences have altered nucleotide sequence relative to the parent sequence, but encode proteins that are essentially identical to the parent sequence. See, for example, Table 4.

TABLE 4

| Synthetic genes encoding AXMIz proteins | |
|---|---|
| Synthetic sequence | Nucleotide SEQ ID NO: |
| axmi221zv02.02 | 6 |
| axmi222zv02.02 | 7 |
| axmi223zv03.02 | 8 |
| axmi224zv03.02 | 9 |
| axmi225zv02.02 | 10 |
| axmi221zv02.03 | 11 |
| axmi222zv02.03 | 12 |
| axmi223zv03.03 | 13 |
| axmi224zv03.03 | 14 |
| axmi225zv02.03 | 15 |
| axmi221zv02.04 | 16 |
| axmi222zv02.04 | 17 |
| axmi223zv03.04 | 18 |
| axmi224zv03.04 | 19 |
| axmi225zv02.04 | 20 |

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENBANK® ID GI:14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif, SEQ ID NO:33) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the amino acid sequence of the invention, as well as the KDEL sequence at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

Example 6. Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

DN62A5S Media

| Components | Per Liter | Source |
| --- | --- | --- |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 7. Transformation of Genes of the Invention in Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A construct comprising a nucleotide sequence operably linked to a heterologous promoter and encoding an amino acid sequence having pesticidal activity against lepidopteran or coleopteran pests, wherein said nucleotide sequence is selected from the group consisting of:
   a) the nucleotide sequence set forth in SEQ ID NO:1 or 6; and
   b) a nucleotide sequence that encodes a polypeptide comprising the amino acid sequence of SEQ ID NO: 21 or 23.

2. The construct of claim 1, wherein said nucleotide sequence is a synthetic sequence that has been designed for expression in a plant.

3. The construct of claim 1, wherein said promoter is capable of directing expression of said nucleotide sequence in a plant cell.

4. A vector comprising the construct of claim 1.

5. The vector of claim 4, further comprising a nucleic acid molecule encoding a heterologous polypeptide.

6. A host cell that contains the vector of claim 4.

7. The host cell of claim 6 that is a bacterial host cell.

8. The host cell of claim 6 that is a plant cell.

9. A transgenic plant comprising the host cell of claim 8.

10. The transgenic plant of claim 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. A transgenic seed comprising the construct of claim 1.

12. A recombinant polypeptide with pesticidal activity wherein said polypeptide comprises the amino acid sequence of SEQ ID NO: 21 or 23,
wherein said polypeptide further comprises a chloroplast transit peptide.

13. A composition comprising the polypeptide of claim 12.

14. The composition of claim 13, wherein said composition is selected from the group consisting of a powder, dust, pellet, granule, spray, emulsion, colloid, and solution.

15. The composition of claim 13, wherein said composition is prepared by desiccation, lyophilization, homogenization, extraction, filtration, centrifugation, sedimentation, or concentration of a culture of bacterial cells.

16. The composition of claim 13, comprising from 1% to 99% by weight of said polypeptide.

17. A method for controlling a lepidopteran or coleopteran pest population comprising contacting said population with a pesticidally effective amount of the polypeptide of claim 12.

18. A method for killing a lepidopteran or coleopteran pest, comprising contacting said pest with, or feeding to said pest, a pesticidally effective amount of the polypeptide of claim 12.

19. A method for producing a polypeptide with pesticidal activity, comprising culturing the host cell of claim 6 under conditions in which the nucleic acid molecule encoding the polypeptide is expressed.

20. A plant having stably incorporated into its genome a DNA construct comprising a nucleotide sequence that encodes a protein having pesticidal activity against lepidopteran or coleopteran pests, wherein said nucleotide sequence is selected from the group consisting of:
   a) the nucleotide sequence set forth in SEQ ID NO:1 or 6; and
   b) a nucleotide sequence that encodes a polypeptide comprising the amino acid sequence of any of SEQ ID NO: 21 or 23.

21. A method for protecting a plant from a pest, comprising expressing in a plant or cell thereof a nucleotide sequence that encodes a polypeptide having pesticidal activity against a lepidopteran or a coleopteran pest, wherein said nucleotide sequence is selected from the group consisting of:
   a) the nucleotide sequence set forth in SEQ ID NO:1 or 6; and
   b) a nucleotide sequence that encodes a polypeptide comprising the amino acid sequence of any of SEQ ID NO: 21 or 23.

22. The method of claim 21, wherein said plant produces a pesticidal polypeptide having pesticidal activity against a lepidopteran or a coleopteran pest.

23. A method for increasing yield in a plant comprising growing in a field a plant or a seed thereof having stably incorporated into its genome a DNA construct comprising a nucleotide sequence that encodes a protein having pesticidal activity against lepidopteran or coleopteran pests, wherein said nucleotide sequence is selected from the group consisting of:
   a) the nucleotide sequence set forth in SEQ ID NO:1 or 6; and
   b) a nucleotide sequence that encodes a polypeptide comprising the amino acid sequence of any of SEQ ID NO: 21 or 23;
wherein said field is infested with a pest against which said polypeptide has pesticidal activity and wherein said yield is increased relative to the yield of a plant not comprising said nucleotide sequence.

* * * * *

SEQUENCE LISTING

```
<160> NUMBER OF SEQ ID NOS: 33

<210> SEQ ID NO 1
<211> LENGTH: 3687
<212> TYPE: DNA
<213> ORGANISM: Bacillus thuringiensis

<400> SEQUENCE: 1
atgaatcaaa ataaacacgg aattattggc gcttccaatt gtggttgtac gtcagataat     60
gttgcgaaat atcctttagc caacaatcca tattcatctg ctttaaattt aaattcttgt    120
caaaatagta gtattctcaa ctggattaac ataataggcg atgcagcaaa agaagcagta    180
tctattggga caacaatagt ctctcttatc acagcacctt ctcttactgg attaatttca    240
atagtatatg accttatagg taaagtacta ggaggtagta gtggccaatc catatcagat    300
ttgtctatat gtgacttatt atctattatt gatttgcggg taaatcagag tgttttaaat    360
gatgggattg cagattttaa tggttctgta ctcttataca ggaactattt agaggctctg    420
gatagctgga ataagaatcc taattctgct tctgctgaag aactccgtac tcgttttaga    480
atcgctgact cagaatttga tagaatttta acacgagggt ctttaacgaa tggtggctcg    540
ttagctagac aaaatgccca aatattatta ttaccttctt ttgcgagtgc tgcatttttc    600
catttattac tactaaggga tgctactaga tatggcacta attgggggct atacaatgct    660
acacctttta taaattatca atcaaaacta gtagagctta ttgaactata tactgattat    720
tgcgtacatt ggtataatcg aggtttcaac gaactaaggc aacgaggcac tagtgctaca    780
gcttggttag aatttcatag atatcgtaga gagatgacat tgatggtatt agatatagta    840
gcatcatttt caagtcttga tattactaat tacccaatag aaacagattt tcagttgagt    900
agggtcattt atacagatcc aattggtttt gtacatcgta gtagtcttag gggagaaagt    960
tggtttagct ttgttaatag agctaatttc tcagatttag aaaatgcaat acctaatcct   1020
agaccgtctt ggtttttaaa taatatgatt atatctactg gttcacttac attgcccgtt   1080
agtccaaata ctgatagagc gagagtatgg tatgggagcc gagatagaat ttcccctgct   1140
aattcacaag taatttctga gctgatttcg gggcaacata cgaattctac acaaactatt   1200
ttagggcgaa atatatttag aatagattct caagcatgta atttaaatga taccacatat   1260
ggagtaaaca gggctgtatt ttatcatgat gctagtgaag gttctcaaag atcagtgtac   1320
gaagggttta ttagaacaac tggaatagat aatcctagag ttcagaatat taatacttat   1380
tttcctggag aaaattcaaa tatcccaact ccagaagact atactcattt attaagtaca   1440
acagtaaatt taacaggagg tcttagacaa gtagcaaata atcgtcgttc atctatagta   1500
atttatggtt ggacacataa aagtctaact cgtaacaata ctattaatcc aggtattatt   1560
acacaaatcc caatggttaa attatccaat ctcccttcag gtactaatgt tgttagaggg   1620
ccaggattta caggtggaga tatccttcgt agaacgaatg ctggtaactt tggagatgta   1680
cgagtcaata ttgctggatc attatcccaa agatatcgcg taaggattcg ttatgcttct   1740
actacaaatt tacaattcca cacatcaatt aacggaagag ctattaatca agcgaatttt   1800
ccagcaacta tgaatatagg tgctagctta aactatagaa cctttagaac tgtaggattt   1860
acaactccat ttactttttc agaagcatca agcatattta cattaagtac tcattccttc   1920
agttcaggca atgcagttta tatagatcga attgaatttg tcccggcaga agtaacattc   1980
gaggcagaat ctgatctaga aagagcacag aaggcggtga atgcgctgtt tacttcttcc   2040
aatcaaatcg gcttaaaaac agatgtgacg gactatcata ttgatcaagt ttccaattta   2100
```

```
gttgcgtgtt tatcggatga attttgtctg gatgaaaagc gagagttgtc cgagaaagtc    2160
aaacatgcga agcgactcag tgatgagcga aatttacttc aagatccaaa cttcagaggc    2220
atcaatagac aactagaccg tggttggaga ggaagtacgg atattaccat ccaaggtgga    2280
gatgacgtat tcaaagagaa ttacgtcaca ctgccgggta cctttgatga gtgctatcca    2340
acatatttat atcaaaaaat agatgagtcg aaattaaaag cctatacccg ctatgaatta    2400
agagggtata ttgaagatag tcaagactta gaagtctatt tgatccgtta caatgcaaaa    2460
cacgaaacgt taaatgtgcc aggtacgggt tccttatggc cacttgcagc cgaaagttca    2520
atcgggaggt gcggcgaacc gaatcgatgc gcgccacata ttgaatggaa tcctgaccta    2580
gattgttcgt gtagggatgg agaaaaatgt gcacatcatt ctcatcattt ctccttggat    2640
attgatgttg gatgtacaga cttaaatgag gatttaggtg tatgggtgat attcaagatt    2700
aagacgcaag atggccacgc aagacttgga aatctagagt ttctcgaaga gaaaccatta    2760
ttaggagaag cgctagctcg tgtgaagaga gcggagaaaa aatggagaga caaacgcgac    2820
aaattggaat tggaaacaaa tattgtttat aaagaggcaa agaatctgt agatgcttta    2880 ttcgtagatt ctcaatataa tagattacaa acggatacga acattgcgat gattcatgcg    2940
gcagataaac gcgttcatcg aatccgagaa gcgtatctgc cagagttgtc tgtaattccg    3000
ggtgtcaatg cggctatttt cgaagaatta gaaggtctta ttttcactgc attctcccta    3060
tatgatgcga gaaatgtcat taaaaacgga gatttcaatc atggtttatc atgctggaac    3120
gtgaaagggc atgtagatgt agaagaacaa aataaccacc gttcggtcct tgttgtcccg    3180
gaatgggagg cagaagtgtc acaagaagtc cgcgtatgtc caggacgtgg ctatatcctg    3240
cgtgtcacag cgtacaaaga gggctacgga gaaggatgcg taacgatcca tgaaattgaa    3300
gatcatacag acgaactgaa atttagaaac tgtgaagaag aggaagggta tccaaataac    3360
acggtaacgt gtaatgatta tactgcgaat caagacgaat acaagggtgc gtacccttct    3420
cgtaatggtg gatatgagga tacatatgac acttcagcat ctgttcatta caacacacca    3480
acgtacgaag aagaaatagg aacagatcta cagagatata atcagtgtga aaataacaga    3540
ggatatggaa attacacacc actaccagca ggttatgtaa caaagaatt agagtacttc    3600 ccagaaacag ataagtatg gatagagatt ggcgaaacgg aaggaacatt catccgtagac    3660 agtgtggaat tactcctcat ggaggaa                                         3687
```

<210> SEQ ID NO 2
<211> LENGTH: 3711
<212> TYPE: DNA
<213> ORGANISM: Bacillus thuringiensis

<400> SEQUENCE: 2

```
ttgaattcaa ataggaaaaa tgagaacgaa attatagatg cttcatttat tcccgcagta     60
tccaatgagt ctgttacaat ctctaaagaa tatgcacaaa caaatcaatt acaaaacaat    120
agcattgagg atggtttgtg tatagccgaa ggggaatata ttgatccatt tgttagcgca    180
tcaacagtcc aaacggggat tagtatcgct ggtagaatat tgggtgtatt aggtgtgccg    240
tttgccggac aattagctag tttttatagt tttattgttg gtgaattatg gcctaaaggc    300
agagaccaat gggaaatttt tatggaacat gtagaacaac ttgtaagaca acaaataaca    360
gcaaatgcta ggaatacggc ccttgctcga ttacaaggtt taggagattc ctttagagcc    420
tatcaacagt cacttgaaga ttggctagag aaccgtaatg atgcaagaac gagaagtgtt    480
```

-continued

```
ctttatactc aatatatagc cttagagctt gattttctaa atgcgatgcc gcttttcgca     540
ataagagagc aagaggttcc cttattaatg gtatacgctc aagctgcaaa cttgcaccta     600
ttattattga gagacgcctc cctttatggt cgtgaatttg ggcttacctc ccaagaaatt     660
caacgttatt atgaacgcca agtagaaaga acgagggact attctgacca ttgcgtgcaa     720
tggtataata cgggtctaaa taacttaaga gggacaaatg ctgaaagttg ggtgcggtat     780
aatcaattcc gtagagacct aacattaggg gtattagatc tagtggcact attcccaagc     840
tatgacactc gcacttatcc aataaatacg agtgctcagt taacaaggga gtttataca      900 gacgcaattg gagcaacagg ggtaaatatg gcaagtatga attggtataa taataatgca     960
ccttcgtttt ccgctataga gactgcggtt atccgaagcc cgcatctact tgattttcta    1020
gaacaactta aaattttag cgcttcatca cgatggagta atactaggca tatgacttat     1080 tggcggggggc acacgattca atctcggcca ataagagggg cattaattac ctcgacacac    1140
ggaaatacca atacttctat taaccctgta acattccagt tcccgtcccg agacgtttat    1200
aggactgaat catatgcagg agtgcttcta tggggaattt accttgaacc tattcatggt    1260
gttcctactg ttagatttaa ttttaggaac cctcagaata cttttgaaag aggtactgct    1320
aactatagtc aaccctatga gtcacctggg cttcaattaa aagattcaga aactgaatta    1380
ccaccagaaa caacagaacg accaaattat gaatcatata gtcatagatt atctcacata    1440
gggatcattt tacaaactag gttgaatgta ccggtatatt cttggacgca cgtagtgca    1500 gatcgtacaa atacaattgg accaaataga attactcaaa ttcctgcagt gaagggaaac    1560
cttcttttta atggttctgt aatttcagga ccaggattta ctggtgggga cttagttaga    1620
ttaaataata gtggaaataa tattcaaaat agaggctatc ttgaggttcc aattcaattc    1680
acatcgacat ctaccagata tcgagttcgt gtacgttatg cttctgtaac cccgattcac    1740
ctcagtgtta attggggtaa ttcaaacatt ttttccagca cagttccagc tacagctgcg    1800
tcattagata atctacaatc aagggatttt ggttattttg aaagtaccaa tgcatttaca    1860
tctgtaacag gtaatgtagt aggtgtaaga aattttagtg aaaatgccag agtgataata    1920
gacagatttg aatttattcc agttactgca accttcgaag cagaatacga tttagaaagg    1980
gcgcaagagg cggtgaatgc tctgtttact aatacgaatc caagaagatt gaaaacagat    2040
gtgacagatt atcatattga tcaagtatcc aatttagtgg cgtgtttatc ggatgaattc    2100
tgcttagatg aaaagagaga attacttgag aaagtgaaat atgcgaaacg actcagtgat    2160
gaaagaaact tactccaaga tccaaaactt c acatccatca ataagcaacc agacttcata   2220
tctactaatg agcaatcgaa tttcacatct atccatgaac aatctgaaca tggatggtgg    2280
ggaagtgaga acattacaat ccaggaagga aatgacgtat ttaaagagaa ttacgtcaca    2340
ctaccaggta cttataatga gtgttatccg acgtatttat atcaaaaaat aggagagtcg    2400
gaattaaaag cttatactcg ctaccaatta agaggttata ttgaagatag tcaagattta    2460
gagatatatt tgattcgtta taatgcgaaa catgaaacat tggatgttcc aggtaccgag    2520
tccgtatggc cgctttcagt tgaaagccca atcagaaggt gcggagaacc gaatcgatgc    2580
gcaccacatt ttgaatggaa tcctgatcta gattgttcct gcagagatgg agaaaaatgt    2640
gcgcatcatt cccatcattt ctctttggat attgatgttg gatgcataga cttgcatgag    2700
aacctaggcg tgtgggtggt attcaagatt aagacgcagg aaggtcatgc aagactaggg    2760
aacctggaat ttattgaaga gaaaccatta ttaggagaag cactgtctcg tgtgaagaga    2820
gcagagaaaa aatggagaga caaacgtgaa aaactacaat tggaaacaaa acgagtatat    2880
```

| | |
|---|---|
| acagaggcaa aagaagctgt ggatgcttta tttgtagatt ctcaatatga tagattacaa | 2940 |
| gcggatacaa acattggcat gattcatgcg gcagataaac ttgttcatcg aattcgagag | 3000 |
| gcgtatcttt cagaattatc tgttatccca ggtgtaaatg cggaaatttt tgaagaatta | 3060 |
| gaaggtcgca ttatcactgc aatctcccta tacgatgcga gaaatgtcgt taaaaatggt | 3120 |
| gattttaata atggattagc atgctggaat gtaaaagggc atgtagatgt acaacagagc | 3180 |
| catcaccgtt ctgtccttgt tatcccagaa tgggaagcag aagtgtcaca agcagttcgc | 3240 |
| gtctgtccgg ggcgtggcta tatcctccgt gtcacagcgt acaagaggg atatggagag | 3300 |
| ggttgtgtaa cgatccatga aatcgagaac aatacagacg aactaaaatt taaaaactgt | 3360 |
| gaagaagagg aagtgtatcc aacggataca ggaacgtgta atgattatac tgcacaccaa | 3420 |
| ggtacagcag catgtaattc ccgtaatgct ggatatgagg atgcatatga agttgatact | 3480 |
| acagcatctg ttaattacaa accgacttat gaagaagaaa cgtatacaga tgtacgaaga | 3540 |
| gataatcatt gtgaatatga cagagggtat gtgaattatc caccactacc agctggttat | 3600 |
| gtgacaaagg aattagaata tttcccagaa accgataagg tatggattga gattggagaa | 3660 |
| acggaaggaa cattcatcgt ggacagcata gaattactcc tcatggaaga a | 3711 |

<210> SEQ ID NO 3
<211> LENGTH: 2157
<212> TYPE: DNA
<213> ORGANISM: Bacillus thuringiensis

<400> SEQUENCE: 3

| | |
|---|---|
| atgaaactaa agaatcaaga taagcatcaa agtttttcta gcaatgcgaa agtagataaa | 60 |
| atctctacgg attcactaaa aaatgaaaca gatatagaat tacaaaacat taatcatgaa | 120 |
| gattgtttga aaatgtctga gtatgaaaat gtagagccgt tgttagtgt atcaacaatt | 180 |
| caaacgggta ttggtattgc tggtaaaatc cttggtaacc taggcgttcc ctttgctggg | 240 |
| caagtagcta gcctctatag ttttatccta ggtgagcttt ggcccaaagg gaaaagccaa | 300 |
| tgggaaattt ttatggaaca tgtagaagag cttattaatc aaaaaatatc gacttacgca | 360 |
| agaaacaaag cacttgcaga tttaaaagga ttaggagatg ctttggctgt ctaccatgaa | 420 |
| tcgctggaaa gttggattaa aaatcgcaat aacacaagaa ctagaagtgt tgtcaagagc | 480 |
| caatacatta ccttggaact tatgttcgta caatcattac cttcttttgc agtgtctgga | 540 |
| gaggaagtac cactattacc aatatatgct caagctgcaa atttacactt gttgctatta | 600 |
| agagatgcgt ctattttggg aaaagaatgg ggattatcag actcagaaat ttcgacattc | 660 |
| tataatcgtc aagtggaaag aacatcagat tattccgatc attgcacgaa atggtttgat | 720 |
| acgggcttga atagattaaa gggctcaaat gctgaaatct gggtaaagta taatcaattc | 780 |
| cgtagagaca tgactttaat ggtactagat ttagtggcac tattccaaag ctatgataca | 840 |
| catatgtacc caattaaaac tacagcccaa cttactagag aagtatatac aaacgcaatt | 900 |
| gggacagtac atccgcaccc aagttttgca agtacgactt ggtataataa taatgcacct | 960 |
| tcgtttctg ccatagaggc tgccgttatc cgaagcccgc acctactcga ttttctagaa | 1020 |
| caagttacaa tttacagctt attaagtcga tggagtaaca ctcagtatat gaatatgtgg | 1080 |
| ggaggacata aactagaatt ccgaacaata ggaggaacgt taaatacctc aacacaagga | 1140 |
| tctactaata cttctattaa tcctgtaaca ttaccgttca cgtctcgaga catctatagg | 1200 |
| actgaatcat tggcagggct gaatctattt ttaactcaac ctgttaatgg agtacctagg | 1260 |

```
gttgattttc attggaaatt cgtcacacat ccgatcgcat ctgataattt ctattatcca   1320
gggtatgctg gaattgggac gcaattacag gattcagaaa atgaattacc acctgaaaca   1380
acaggacagc caaattatga atcttatagt catagattat ctcatatagg actcatttca   1440
gcatcacatg tgaaagcatt ggtatattct tggacgcatc gtagtgcaga tcgtacgaat   1500
acaattcatt cagatagtat aacacaaata ccactggtaa aagcacatac ccttcagtca   1560
ggtactactg ttgtaaaagg gccagggttt acaggtggag atatcctccg acgaactagt   1620
ggaggaccat ttgcttttag taatgttaat ttagactgga acttgtcaca aagatatcgt   1680
gctagaatac gctatgcttc tactactaat ctaagaatgt acgtaacgat tgcaggggaa   1740
cgaatttttg ctggtcaatt taataaaaca atgaatactg gtgatccatt aacattccaa   1800
tcttttagtt acgcaactat tgatacagca tttacattcc caacgaaagc gagcagcttg   1860
actgtaggtg ctgatacttt tagctcaggt aatgaagttt atgtagatag atttgaattg   1920
atcccagtta ctgcaacact tgaggcagta actgatttag aaagagcgca gaaggcggtt   1980
catgaactgt ttacatctac gaatccggga ggattaaaaa cggatgtaaa ggattatcat   2040
attgaccagg tatcaaattt agtagagtct ctatcagatg aattctatct tgatgaaaag   2100
agagaattat tcgagatagt taaatacgcg aagcaactcc atattgagcc taacatg      2157
```
<210> SEQ ID NO 4
<211> LENGTH: 1998
<212> TYPE: DNA
<213> ORGANISM: Bacillus thuringiensis

<400> SEQUENCE: 4

```
gtggttgtga ataagtattt tcttaaaaac attcgttatt atcaggctaa tttagtatct     60
ttaattttaa tatataacct aatatttaag gaggaatttt atatgaatag tgtattgaat    120
agcggaagag ctactaatgg tgatgcgtat aatgtagtgg ctcatgatcc atttagtttt    180
caacataaat cattagatac catacaagaa gaatggatgg agtggaaaaa agataatcat    240
agtttatatg tagatcctat tgttggaact gtggctagct ttcttttaaa gaaagtgggg    300
agtcttgttg gaaaaagaat attaagtgag ttacggaatt taatatttcc tagtggcagt    360
acaaatctaa tgcaagatat tttaagagag acagaaaaat tcctgaatca aagacttaat    420
acagacactc ttgcccgtgt aaatgcggaa ttgacagggc tgcaagcaaa tgtagaagag    480
tttaatcgac aagtagataa ttttttgaac cctaaccgaa atgctgttcc tttatcaata    540
acttcttcag ttaatacaat gcagcaatta tttctaaata gattacccca gtttcagatg    600
caaggatacc aattgttatt attaccttta tttgcacagg cagccaattt acatcttttct   660 tttattagag atgttattct taatgcagat gaatggggaa tttcagcagc aacattacgt    720
acgtatcaaa atcacctgag aaattataca agagagtact ctaattattg tataactacg    780
tatcaaactg cgtttagagg tttaaacacc cgtttacacg atatgttaga atttagaaca    840
tatatgtttt taaatgtatt tgaatatgta tctatctggt cgttgtttaa atatcaaagc    900
cttctagtat cttctggtgc taatttatat gcaagtggta gtggaccaca gcagacccaa    960
tcatttactt cacaagactg gccattttta tattctcttt tccaagttaa ttcaaattat   1020
gtgttaaatg gctttagtgg cgctagactt acgcagactt tccctaatat tgttggttta   1080
cctggtacta ctacaactca cgcattgctt gctgcaaggg tcaattacag tggaggagtt   1140
tcgtctggtg atataggcgc tgtgtttaat caaaatttta gttgtagtac atttctccca   1200
cctttgttaa caccatttgt tagaagttgg ctagattcag gttcagatcg gggggggatt   1260
```

```
aataccgtta ccaattggca aacagaatcc tttgagacaa ctttaggttt aaggagtggt   1320
gcttttacag ctcgaggtaa ttcaaactat ttcccagatt attttatccg taatatttct   1380
ggagttcctt tagttgttag aaatgaagat ttaagaagac cgttacacta taatcaaata   1440
agaaatatag aaagtccttc aggaacacct ggtggattac gagcttatat ggtatctgtg   1500
cataacagaa aaaataatat ctatgccgtt catgaaaatg gtactatgat tcatttagcg   1560
ccggaagatt atacaggatt tactatatcg ccgatacatg caactcaagt gaataatcaa   1620
acgcgaacat ttatttctga aaaatttgga aatcaaggtg attccttaag atttgaacaa   1680
agcaacacga cagctcgtta taccettaga gggaatggaa atagttacaa tctttattta   1740
agagtatctt caataggaaa ttccactatt cgagttacta taaacggtag agtttatact   1800
gcttcaaatg ttaatactac tacaaataac gatggagtta atgataatgg agctcgtttt   1860
tcagatatta atatcggtaa tgtagtagca agtgataata ctaatgtacc gttagatata   1920
aatgtgacat taaattcggg tactcaattt gagctgatga atattatgtt tgttccaact   1980
aatagctcac cactttat                                                 1998
```

<210> SEQ ID NO 5
<211> LENGTH: 3531
<212> TYPE: DNA
<213> ORGANISM: Bacillus thuringiensis

<400> SEQUENCE: 5

```
atggataaca atccgaacat caatgaatgc attccttata attgtttaag taaccctgaa     60
gtagaagtat taggtggaga aagaatagaa actggttaca ccccaatcga tatttccttg    120
tcgctaacgc aatttctttt gagtgaattt gttcccggtg ctggatttgt gttaggacta    180
gttgatataa tatggggaat ttttggtccc tctcaatggg acgcatttct tgtacaaatt    240
gaacagttaa ttaaccaaag aatagaagaa ttcgctagga accaagccat ttctagatta    300
gaaggactaa gcaatcttta tcaaatttac gcagaatctt ttagagcgtg ggaagcagat    360
cctactaatc cagcattaag agtagagatg cgtattcaat tcaatgacat gaacagtgcc    420
cttacaaccg ctattcctct tttgcagtt caaaattatc aagttcctct tttatcagta     480
tatgttcaag ctgcaaattt acatttatca gttttgagag atgtttcagt gtttggacaa    540
aggtggggat ttgatgccac gactatcaat agtcgttata atgatttaac taggcttatt    600
ggcaactata cagattatgc tgtacgctgg tacaatacgg gattagagcg tgtatgggga    660
ccggattcta gagattggat aagatataat caatttagaa gagaattaac actaactgta    720
ttagatatcg tttctctatt tccgaactat gatagtagaa cgtatccaat tcgaacagtt    780
tcccaattaa caagagaaat ttatacaaac ccagtattag aagattttaa tggtagtttt    840
cgaggctcgg ctcagggcat agaacaaagt attaggagtc cgcatttgat ggatatactt    900
aatagtataa ccatctatac ggatgctcat aggggttatt attattggtc agggcatcaa    960
ataatggctt ctcctgtcgg tttttcgggg ccagaattca cgtttccgct atatggaacc   1020
atgggaaatg cagctccaca acaacgtatt gttgctcaac taggtcaggg cgtgtataga   1080
acattatcct ctacttttta tagaagtcct tttaatatag ggataaataa tcaacaacta   1140
tctgttcttg acgggacaga atttgcttat ggaacctcct caaatttgcc atccgctgta   1200
tacagaaaaa gcggaacggt agattcgctg gatgaaatac caccacagaa taacaacgtg   1260
ccacctaggc aaggatttag tcatcgatta agccatgttt caatgtttcg ttcaggattt   1320
```

```
agtaatagta gtgtaagtat aataagagct cctatgttct cttggataca tcgtagtgct      1380
gaatttaata atataattcc ttcatcacaa attacacaaa tacctttaac aaaatctact      1440
aatcttggct ctggaacttc tgtcgttaaa ggaccaggat ttacaggagg agatattctt      1500
cgaagaactt cacctggcca gatttcaacc ttaagagtaa atattactgc accattatca      1560
caaagatatc gcgtaagaat tcgttacgct tctactacaa atttacaatt ccatacatca      1620
attgacggaa gacctattaa tcaggggaat ttttcagcaa ctatgagtag tgggagtaat      1680
ttacagtccg gaagctttag gactgcaggt tttactactc cgtttaactt ttcaaatgga      1740
tcaagtgtat ttacgttaag tgctcatgtc ttcaattcag gcaatgaagt ttatatagat      1800
cgaattgaat ttgttccggc agaagtaacc tttgaggcag aatatgattt agaaagagca      1860
cagaaggcgg tgaatgcgct gtttacttct tccaatcaaa tcgggttaaa aacagatgtg      1920
acggattatc atattgatca agtatccaat ttagttgagt gtttatcaga tgaattttgt      1980
ctggatgaaa acaagaatt gtccgagaaa gtcaaacatg cgaagcgact tagtgatgag      2040
cggaatttac ttcaagatcc aaacttcaga gggatcaata gacaactaga ccgtggctgg      2100
agaggaagta cggatattac catccaagga ggcgatgacg tattcaaaga gaattacgtt      2160
acactaccag gtacctttga tgagtgctat ccaacgtatt tatatcaaaa aatagatgag      2220
tcgaaattaa aagcctatac ccgttatcaa ttaagagggt atatcgagga tagtcaagac      2280
ttagaaatct atttaattcg ctacaatgca aaacatgaaa cagtaaatgt gccaggtacg      2340
ggttccttat ggccgctttc agcccaaagt ccaatcggaa agtgtggaga gccgaatcga      2400
tgcgcgccac accttgaatg gaatcctgac ttagattgtt cgtgtaggga tggagaaatg      2460
tgtgcccatc attcgcatca tttctcctta gacattgatg ttggatgtac agacttaaat      2520
gaggacctag tgtatgggt gatctttaag attaagacgc aagatgggca cgcaagacta      2580
gggaatctag agtttctcga agagaaacca ttagtaggag aagcgctagc tcgtgtgaaa      2640
agagcggaga aaaaatggag agacaaacgt gaaaaattgg aatgggaaac aaatatcgtt      2700
tataaagagg caaagaatc tgtagatgct ttatttgtaa actctcaata tgatcaatta      2760
caagcggata cgaatattgc catgattcat gcggcagata acgtgttca tagcattcga      2820 gaagcttatc tgcctgagct gtctgtgatt ccgggtgtca atgcggctat ttttgaagaa      2880
ttagaagggc gtattttcac tgcattctcc ctatatgatg cgagaaatgt cattaaaaat      2940
ggtgatttta ataatggctt atcctgctgg aacgtgaaag ggcatgtaga tgtagaagaa      3000
caaaacaacc accgttcggt ccttgttgtt ccggaatggg aagcagaagt gtcacaagaa      3060
gttcgtgtct gtccgggtcg tggctatatc cttcgtgtca cagcgtacaa ggagggatat      3120
ggagaaggtt gcgtaaccat tcatgagatc gagaacaata cagacgaact gaagtttagc      3180
aactgcgtag aagaggaaat ctatccaaac aacacggtaa cgtgtaatga ttatactgta      3240
aatcaagaag aatacggagg tgcgtacact tctcgtaatc gaggatataa cgaagctcct      3300
tccgtaccag ctgattatgc atcagtctat gaagaaaaat cgtatacaga tggacgaaga      3360
gagaatcctt gtgaatttaa cagagggtat agggattaca cgccactacc agttggttat      3420
gtgacaaaag aattagaata cttcccagaa accgataagg tatggattga gattggagaa      3480
acggaaggaa catttatcgt ggacagcgtg gaattactcc ttatggagga a                3531
```

<210> SEQ ID NO 6
<211> LENGTH: 1986
<212> TYPE: DNA
<213> ORGANISM: Artificial Sequence
<220> FEATURE:
<223> OTHER INFORMATION: synthethic nucleotide sequence encoding
     AXMI221z (axmi221zv02.02)

<400> SEQUENCE: 6

| | |
|---|---|
| atgaaccaga acaagcatgg catcattgga gcaagcaact gtggatgcac cagcgacaat | 60 |
| gttgcaaaat atcctctggc caacaatcct tattcttctg ctctcaacct caacagctgc | 120 |
| cagaacagca gcatcctcaa ctggatcaac atcattggtg atgctgccaa ggaagctgtc | 180 |
| tccatcggca ccaccatcgt cagcttgatc accgcgccat cattgacagg cctcatctcc | 240 |
| atcgtctatg atctcatcgg caaggtgctg gaggaagca gcggccaaag catctccgac | 300 |
| ctctccatct gcgacctcct ctccatcatc gacctccgcg tcaaccagag cgtgctgaat | 360 |
| gatggcattg ctgatttcaa tggatcagtg ctgctgtaca ggaactacct ggaggcgctg | 420 |
| gacagctgga acaagaaccc aaattctgct tctgctgaag agctgaggac aaggttcaga | 480 |
| attgctgatt cagaatttga caggatcttg acaagaggca gcttgacaaa tggaggaagc | 540 |
| ctggcgcggc aaaatgctca gatcctgctg ctgcctcct ttgcttcagc tgccttcttc | 600 |
| cacctgctgc tgctccgtga tgcaacaaga tatggcacca actggggcct ctacaatgcc | 660 |
| accccccttca tcaactacca gagcaagctg gtggagctga tcgagctcta caccgactac | 720 |
| tgcgtccact ggtacaacag aggcttcaat gagctccgcc aaagaggaac atcagcaaca | 780 |
| gcatggctga gttccaccg ctacaggagg gagatgacct tgatggtgct ggacatcgtc | 840 |
| gcctccttct cctccttgga catcaccaac taccccattg aaacagattt ccagctcagc | 900 |
| agggtgatcc acacagatcc aattggcttc gtccacagaa gcagcttgag aggagaaagc | 960 |
| tggttctcct tcgtcaaccg cgccaacttc tcagatctgg agaatgccat ccccaaccca | 1020 |
| aggccaagct ggttcctcaa caacatgatc atcagcactg gaagcctcac ccttcctgtt | 1080 |
| tctccaaaca ctgaccgcgc gcgcgtctgg tatggaagca gggacaggat ctcgccggcc | 1140 |
| aacagccaag tgatctcaga gctcatctcc ggccagcaca ccaacagcac acaaaccatc | 1200 |
| cttggaagga acatcttcag aattgacagc caagcctgca acctcaatga caccacctac | 1260 |
| ggcgtcaacc gcgccgtgtt ctaccatgat gcttcagaag gaagccaaag aagcgtctat | 1320 |
| gaaggcttca tcaggacaac tggcatcgac aacccaaggg tgcaaaacat aaacacctac | 1380 |
| ttccctggag aaaacagcaa catccccacg ccggaggact acacccacct cctctccacc | 1440 |
| accgtcaacc tcaccggcgg cctccgccag gtggccaaca acagaagatc aagcatcgtc | 1500 |
| atctatggat ggacccacaa gagcttgaca agaaataaca ccatcaaccc tggcatcatc | 1560 |
| acccagatcc ccatggtgaa gctctccaac ctgccatcag aacaaatgt ggtgagagga | 1620 |
| cctggcttca ctggaggaga catcttgagg aggacaaatg ctggaaattt tggagatgtc | 1680 |
| cgcgtcaaca ttgctggaag cctctcccag cgctacaggg tgaggatcag atatgcttca | 1740 |
| acaactaacc tccagttcca cacctccatc aatggccgcg ccatcaacca agcaaacttc | 1800 |
| cccgccacca tgaacattgg agcaagcctc aactacagga ccttcagaac tgttggcttc | 1860 |
| accacccccct tcaccttctc agaagcaagc agcatcttca ccctctccac ccacagcttc | 1920 |
| tcctctggaa atgctgtcta catcgacagg attgaatttg ttcctgctga agtcaccttt | 1980 |
| gaagca | 1986 |

<210> SEQ ID NO 7
<211> LENGTH: 1965
<212> TYPE: DNA
<213> ORGANISM: Artificial Sequence
<220> FEATURE:
<223> OTHER INFORMATION: synthethic nucleotide sequence encoding
     AXMI222z (axmi222zv02.02)

<400> SEQUENCE: 7

```
atgaacagca acaggaagaa tgaaaatgag atcattgatg cttccttcat ccccgccgtc     60
agcaatgaga gcgtcaccat cagcaaggaa tatgctcaaa caaaccagct gcaaaacaac    120
agcattgaag atggcctctg cattgctgaa ggagaataca tagatccatt tgtttcagca    180
agcaccgtcc aaactggcat cagcattgct ggaagaatcc tcggcgtcct cggcgtcccc    240
ttcgccggcc agctggcatc attctacagc ttcattgttg gagagctctg gccaaaagga    300
agagatcaat gggagatctt catggagcat gttgagcagc tggtgaggca gcagatcacc    360
gccaatgcaa ggacaccgc gctggcaagg ctgcaaggcc tcggcgacag cttccgcgcc     420
taccagcaga gcttggagga ctggctggag aacagaaatg atgcaaggac aagatcagtg    480
ctgtacaccc agtacattgc tctggagctg gacttcctca atgccatgcc gctcttcgcc    540
atcagggagc aggaggtgcc gctgctgatg gtgtatgctc aagctgccaa cctccacctg    600
ctgctgctga gagatgcttc attgtatgga agagaatttg gcctcaccag ccaggagatc    660
caaagatatt atgaaaggca ggtggagagg acaagagatt attcagatca ttgtgttcaa    720
tggtacaaca ccggcctcaa caacctccgc ggcaccaatg ctgaaagctg ggtgagatac    780
aaccagttca gaagagatct caccctcggc gtgctggatc tggtggcgct cttcccaagc    840
tatgacacaa ggacatatcc catcaacacc tcagctcagc tgacaaggga ggtgtacaca    900
gatgccattg gagccaccgg cgtcaacatg gcatcaatga actggtacaa caacaatgct    960
ccttccttct ccgccattga aactgctgtc atcagatctc ctcatctgct ggacttcctg   1020
gagcagctga gatcttctc cgcctcctca agatggagca cacaaggca catgacatat    1080
tggagaggcc acaccatcca gagcaggccc atccgcggcg cgctcatcac ctccacccat   1140
ggtaacacca cacctccat caaccccgtc accttccagt tcccttcaag agatgtctac    1200
aggacagaaa gctatgctgg agtgctgctc tggggcatct acctagagcc catccatgga   1260
gttcccaccg tccgcttcaa cttcagaaat cctcaaaaca cctttgaaag aggaacagca   1320
aactacagcc agccatatga atctcctggc ctccagctga aggattcaga aacagagctg   1380
ccgccggaga caacagaaag gccaaactat gaaagctaca gccaccgcct cagccacatc   1440
ggcatcatcc tccaaacaag gctgaatgtt cctgtctaca gctggaccca ccgctctgct   1500
gacaggacca acaccatcgg ccccaacagg atcacccaga tccccgccgt caagggcaac   1560
ctcctcttca atggcagcgt catctcagga cctggcttca ctggaggaga tctggtgagg   1620
ctcaacaaca gcggcaacaa catccagaac agaggctatc ttgaggtgcc catccagttc   1680
acctccacca gcacaagata ccgcgtccgc gtcagatatg cttcagtgac gcccatccac   1740
ctctccgtca actggggcaa cagcaacatc ttctcctcca ccgtgccggc caccgccgcc   1800
tccttggaca accttcaaag cagagatttt ggatattttg aaagcaccaa tgccttcacc   1860
tccgtcactg gaaatgtggt gggcgtcagg aacttctcag aaaatgcaag ggtgatcatc   1920
gacagatttg agttcatccc cgtcaccgcc acctttgaag ctgaa                   1965
```

<210> SEQ ID NO 8
<211> LENGTH: 1797
<212> TYPE: DNA
<213> ORGANISM: Artificial Sequence
<220> FEATURE:
<223> OTHER INFORMATION: synthethic nucleotide sequence encoding AXMI223z (axmi223zv03.02)

<400> SEQUENCE: 8

| | | | | | | |
|---|---|---|---|---|---|---|
| atgtcagaat | atgaaaatgt | ggagccattt | gtttctgtct | ccaccatcca | aactggcatc | 60 |
| ggcattgctg | gcaagatcct | cggcaacctc | ggcgtcccct | tcgccggcca | ggtggcctcc | 120 |
| ctctacagct | tcatcctagg | agagctctgg | ccaaaaggaa | aaagccaatg | ggagatcttc | 180 |
| atggagcatg | ttgaggagct | catcaaccag | aagatctcaa | catatgcaag | gaacaaggcg | 240 |
| ctggcagatc | tgaagggcct | ggagatgct | ctcgccgtct | accatgagag | cttggagagc | 300 |
| tggatcaaga | acaggaacaa | cacaaggaca | aggagcgtgg | tgaagagcca | gtacatcacc | 360 |
| ttggagctga | tgtttgttca | gagcttgccc | tccttcgccg | tgtcaggaga | agaagttcct | 420 |
| ctgctgccca | tctatgctca | agctgctaac | ctccacctgc | tgctgctgag | agatgcttcc | 480 |
| atcttcggca | aggaatgggg | cctctcagat | tcagagatct | ccaccttcta | caacaggcag | 540 |
| gtggagagga | catcagatta | ttcagatcat | tgcaccaaat | ggttcgacac | cggcctcaac | 600 |
| aggctgaagg | gcagcaatgc | tgagatctgg | gtgaagtaca | accagttcag | aagggacatg | 660 |
| accttgatgg | tgctggatct | ggtggcgctc | ttccaatcat | atgacaccca | catgtacccc | 720 |
| atcaagacaa | cagctcagct | gacaagggag | gtgtacacca | atgccatcgg | caccgtccat | 780 |
| cctcatcctt | ccttcgcctc | caccacctgg | tacaacaaca | atgctccttc | cttctccgcc | 840 |
| attgaagctg | ctgtcatcag | atctcctcat | ctgctggact | cctggagca | ggtcaccatc | 900 |
| tacagcctcc | tctcaagatg | gagcaacacc | cagtacatga | acatgtgggg | aggccacaag | 960 |
| ctggagttca | gaaccattgg | aggaaccctc | aacacctcca | cccaaggaag | caccaacacc | 1020 |
| tccatcaacc | ccgtcaccct | ccccttcacc | tcacgtgaca | tctacaggac | agaaagcctc | 1080 |
| gccggcctca | acctcttcct | cacccagcct | gtcaatggag | ttccaagggt | ggacttccac | 1140 |
| tggaagtttg | tgacacatcc | aattgcttct | gacaacttct | actaccctgg | atatgctggc | 1200 |
| atcggcaccc | agctgcaaga | ttcagaaaat | gagctgccgc | cggagacaac | agggcagcca | 1260 |
| aactatgaaa | gctacagcca | ccgcctcagc | cacatcggcc | tcatctcagc | aagccatgtg | 1320 |
| aaggcgctgg | tgtacagctg | gacccaccgc | tccgccgaca | ggaccaacac | catccattct | 1380 |
| gacagcatca | cccagatccc | gctggtgaag | gctcacaccc | tccagagcgg | caccaccgtg | 1440 |
| gtgaaggggc | caggcttcac | tggaggagac | atcttgagaa | gaacatcagg | aggcccttc | 1500 |
| gccttcagca | atgtcaacct | tgattggaac | ctctcccaaa | gatacagagc | aagaatccgc | 1560 |
| tatgcttcca | ccaccaactt | gaggatgtat | gtcaccattg | ctggagaaag | gatcttcgcc | 1620 |
| ggccagttca | acaagaccat | gaacactgga | gatcctctca | ccttccagag | cttctcatat | 1680 |
| gccaccattg | acaccgcctt | caccttcccc | accaaggcca | gcagcctcac | cgtcggcgct | 1740 |
| gacaccttct | cctctggaaa | tgaagtttat | gtggacagat | ttgagctcat | ccctgtt | 1797 |

<210> SEQ ID NO 9
<211> LENGTH: 1896
<212> TYPE: DNA
<213> ORGANISM: Artificial Sequence
<220> FEATURE:
<223> OTHER INFORMATION: synthethic nucleotide sequence encoding
    AXMI224z (axmi224zv03.02)

<400> SEQUENCE: 9

| | | | | | | |
|---|---|---|---|---|---|---|
| atgaacagcg | tcctcaactc | cggccgcgcc | accaatggag | atgcctacaa | tgtggtggct | 60 |
| catgatccct | tctccttcca | gcacaagagc | ttggacacca | tccaagaaga | atggatggaa | 120 |

-continued

```
tggaagaagg acaaccacag cctctatgtt gatccaattg ttggcaccgt cgcctccttc      180
ctgctgaaga aggtgggcag cttggtgggg aagaggatct tgtcagagct gaggaacctc      240
atcttccctt ctggaagcac aacttgatg caagacatcc tcagagaaac agagaagttc       300
ctcaaccagc gcctcaacac cgacaccttg gcgcgcgtca atgctgagct caccggcctt      360
caagcaaatg tggaggagtt caacaggcag gtggacaact tcctcaaccc aaatagaaat      420
gctgttcctc tctccatcac cagctcagtg aacaccatgc agcagctctt cctcaacagg      480
ctgccgcagt tccagatgca aggctaccag ctgctgctgc tgccgctctt tgctcaagct      540
gccaacctcc acctctcctt catcagagat gtcatcctca atgctgatga atggggcatc      600
tccgccgcca ccttgaggac atatcaaaac cacctgagga actacacaag agaatattca      660
aactactgca tcaccaccta ccaaacagcc ttcagaggcc tcaacacaag gctgcatgac      720
atgctggagt tcagaacata catgttcctc aatgttttg aatatgtctc catctggagc       780
ctcttcaagt accagagctt gctggtgagc tctggagcaa acctctatgc ttctggaagc      840
ggcccccagc aaacccagag cttcacctca aagattggc ccttcctcta cagcctcttc       900
caggtgaaca gcaactatgt gctgaatggc ttctctggag caaggctcac ccaaaccttc      960
cctaacatcg tcggccttcc tggcaccacc accacccatg ctctgctggc ggcgcgcgtc      1020
aactactctg gaggagtttc ttctggagac atcggcgcgg tgttcaacca gaacttctca     1080
tgctccacct tcctgccgcc gctgctgacg cccttcgtca gaagctggct ggattctgga      1140
tctgatcgag gaggcatcaa caccgtcacc aactggcaaa cagagagctt gaaacaacc      1200 ttggggctga gaagtggagc cttcacagca agaggaaaca gcaactactt ccccgactac      1260
ttcatcagga acatctcagg agttcctctg gtggtgagaa atgaagatct ccgccggccg      1320
ctccactaca accagatcag gaacattgaa tctccatcag gaactcctgg aggcctccgc      1380
gcctacatgg tgagcgtcca acaggaag aacaacatct atgctgttca tgaaaatggc       1440
accatgatcc atcttgctcc agaagattac accggcttca ccatctcccc catccatgcc      1500
acccaggtga caaccaaac aaggaccttc atctcagaga gtttggaaa tcaaggagac       1560 agcttgagat ttgagcagag caacaccacg gcgcgctaca ccctccgcgg caatggcaac      1620
agctacaacc tctacctccg cgtcagcagc atcggcaaca gcaccatcag ggtgaccatc      1680
aatggccgcg tctacaccgc cagcaatgtc aacaccacca caacaatga tggcgtcaat       1740 gacaatggag caaggttctc agacatcaac attggaaatg tggtggcctc gacaacacc       1800 aatgttcctc tggacatcaa tgtcaccctc aacagcggca cccagttcga gctgatgaac      1860
atcatgtttg ttccaacaaa cagctcgccg ctgtac                                1896
```

<210> SEQ ID NO 10
<211> LENGTH: 1821
<212> TYPE: DNA
<213> ORGANISM: Artificial Sequence
<220> FEATURE:
<223> OTHER INFORMATION: synthethic nucleotide sequence encoding
    AXMI225z (axmi225zv02.02)

<400> SEQUENCE: 10

```
atggacaaca accccaacat caatgaatgc atcccctaca actgcttgag caacccagag       60
gtggaggtgc tgggaggaga aaggattgaa actggctaca ccccatcga catctccctc      120 tccctcaccc agttcctcct ctcagaattt gttcctggag ctggcttcgt gctggggctg      180
gtggacatca tctctgggcat cttcggccct tctcaatggg atgccttcct cgtccagatc      240
```

-continued

| | |
|---|---|
| gagcagctga tcaaccagag gattgaagaa tttgcaagga accaggccat ctcaaggctg | 300 |
| gaaggcctct ccaacctcta ccagatctat gctgagagct tccgcgcctg ggaagcagat | 360 |
| ccaacaaatc ctgctctccg cgtggagatg aggattcagt tcaatgacat gaactcagct | 420 |
| ctcaccaccg ccatccctct cttcgccgtc cagaactacc aggtgccgct gctctccgtc | 480 |
| tatgttcaag ctgccaacct ccacctctcc gtgctgagag atgtttcagt ttttggccaa | 540 |
| agatggggct tgatgccac caccatcaac agcagataca atgatctgac aaggctcatc | 600 |
| ggcaactaca cagattatgc tgtcagatgg tacaacaccg gcctggagcg cgtctggggg | 660 |
| ccagattcaa gagattggat cagatacaac cagttcagaa gggagctcac cttgacggtg | 720 |
| ctggacatcg tcagcctctt ccccaactat gattcaagga catatcccat caggaccgtc | 780 |
| agccagctga aagggagat ctacaccaac cccgtgctgg aggacttcaa tggcagcttc | 840 |
| agaggatcag ctcaaggcat cgagcagagc atcagatctc ctcatctgat ggacatcctc | 900 |
| aacagcatca ccatctacac tgatgctcac cgcggctact actactgag cggccaccag | 960 |
| atcatggctt ctcctgttgg cttctcagga cctgagttca ccttccctct ctatggcacc | 1020 |
| atgggcaacg ccgcgccgca gcagaggatc gtcgcccagc tgggccaagg cgtctacagg | 1080 |
| accttgagca gcaccttcta cagaagcccc ttcaacatcg gcatcaacaa ccagcagctc | 1140 |
| tccgtgctgg atggaactga atttgcatat ggaacaagca gcaaccttcc ttcagctgtc | 1200 |
| tacaggaaga gcggcaccgt ggacagcttg gatgagatcc cgccgcagaa caacaatgtg | 1260 |
| ccgccgcgcc aaggcttcag ccaccgcctc agccatgtga gcatgttcag aagcggcttc | 1320 |
| agcaacagca gcgtcagcat catccgcgcg ccgatgttca gctggattca ccgctctgct | 1380 |
| gagttcaaca acatcatccc ttcttcacag atcacccaga tccccctcac caagagcacc | 1440 |
| aacctcggca gcggcacctc cgtggtgaag gggccaggct tcactggagg tgacatcttg | 1500 |
| aggaggacat ctcctggcca gatctccacc ctccgcgtca acatcaccgc gccgctctct | 1560 |
| caaagataca gggtgaggat cagatatgct tcaacaacaa acctccagtt ccacaccagc | 1620 |
| attgatggcc gccccatcaa tcaaggaaac ttctccgcca ccatgagctc aggaagcaac | 1680 |
| ctccagagcg gcagcttcag aactgctggc ttcaccaccc ccttcaactt cagcaatgga | 1740 |
| agctccgtgt tcaccctctc tgctcatgtt ttcaacagcg gcaatgaggt gtacatcgac | 1800 |
| aggattgaat tgttccagc a | 1821 |

<210> SEQ ID NO 11
<211> LENGTH: 1986
<212> TYPE: DNA
<213> ORGANISM: Artificial Sequence
<220> FEATURE:
<223> OTHER INFORMATION: synthethic nucleotide sequence encoding
AXMI221z (axmi221zv02.03)

<400> SEQUENCE: 11

| | |
|---|---|
| atgaatcaaa acaaacatgg aatcattgga gcttcaaatt gtggatgcac ttcagacaat | 60 |
| gttgcaaaat atcctcttgc aaacaattcca tattcttctg ctttgaatct caattcttgt | 120 |
| caaaattctt caattttgaa ttggatcaac atcattggtg atgctgcaaa agaagctgtt | 180 |
| tcaattggaa caacaattgt ttctttgatc actgctcctt ctttgactgg attgatttca | 240 |
| attgtttatg atttgattgg aaaagttctt ggaggaagtt ctggacaaag catttctgat | 300 |
| ctttcaattt gtgatcttct ttcaatcatt gatttgagag tgaatcaaag tgttttgaat | 360 |
| gatggaattg ctgatttcaa tggaagtgtt cttctttaca gaaattattt ggaagcattg | 420 |

```
gattcttgga caagaatcc aaattctgct tctgctgaag aattgagaac aagattcaga      480
attgctgatt cagaatttga cagaattttg acaagaggaa gtttgacaaa tggaggaagt      540
ttggcaagac aaaatgctca aattcttctt cttccttctt ttgcttctgc tgctttcttt      600
catttgttgt tgttgagaga tgcaacaaga tatggaacaa attggggatt gtacaatgca      660
acaccattca tcaattatca atcaaaattg gtggaattga ttgaacttta cactgattat      720
tgtgttcatt ggtacaacag aggattcaat gaattgagac aaagaggaac ttctgcaact      780
gcttggttgg aatttcacag atacagaaga gaaatgacat tgatggtttt ggatattgtt      840
gcttcttttt cttctttgga catcacaaat tatccaattg aaacagattt tcaactttca      900
agagtgattt acactgatcc aattggattt gttcacagaa gttctttgag aggagaaagt      960
tggttttctt ttgtcaacag agcaaatttt tcagatttgg aaaatgcaat tccaaatcca     1020
agaccttctt ggtttctcaa caacatgatc atttcaactg aagtttgac acttcctgtt     1080 tctccaaaca ctgacagagc aagagtttgg tatggaagca gagacagaat ttctccagca     1140
aattctcaag tgatttcaga attgattct ggacaacaca caaattcaac tcaaacaatt     1200
cttggaagaa acatttcag aattgattct caagcatgca atttgaatga tacaacatat     1260
ggagtgaaca gagctgtttt ttatcatgat gcttcagaag gaagccaaag aagtgtttat     1320
gaaggattca tcagaacaac tggaattgac aatccaagag ttcaaaacat caacacatat     1380
tttcctggag aaaattcaaa cattccaaca ccagaagatt acactcatct tctttcaaca     1440
actgttaatt tgactggagg attgagacaa gttgcaaaca cagaagaag ttcaattgtg      1500 atttatggat ggacacacaa aagtttgaca agaaacaaca caatcaatcc tggaatcatc     1560
actcaaattc caatggtgaa actttcaaat cttccttctg gaacaaatgt tgttagagga     1620
cctggattca ctggtggaga tattttgaga gaaacaaatg ctggaaattt tggagatgtg     1680
agagtgaaca ttgctggttc tcttttctcaa agatacagag tgagaatcag atatgcttca     1740
acaacaaatc ttcaatttca cacttcaatt aatggaagag caatcaatca agcaaatttt     1800
cctgcaacaa tgaacattgg agcttctttg aattacagaa cttccagaac tgttggattc     1860
acaacaccat tcacattttc agaagcaagt tcaattttca ctctttcaac tcattctttt     1920
tcttctggaa atgctgttta cattgacaga attgaatttg ttcctgctga agtgacattt     1980
gaagca                                                                1986

<210> SEQ ID NO 12
<211> LENGTH: 1965
<212> TYPE: DNA
<213> ORGANISM: Artificial Sequence
<220> FEATURE:
<223> OTHER INFORMATION: synthethic nucleotide sequence encoding
      AXMI222z (axmi222zv02.03)

<400> SEQUENCE: 12
atgaactcaa acagaaagaa tgaaaatgaa atcattgatg cttctttcat tcctgctgtt       60
tcaaatgaaa gtgtgacaat ttcaaaagaa tatgctcaaa caaatcaact tcaaaacaat      120
tcaattgaag atggattgtg cattgctgaa ggagaatata ttgatccatt tgtttctgct      180
tcaacagttc aaactggaat aagcattgct ggaaggattc ttggagttct ggagttcca      240 tttgctggac aacttgcttc attttattct ttcattgttg agaattgtg gccaaaagga      300 agagatcaat gggaatttt catggaacat gttgaacaat ggtgagaca acaaatcact      360 gcaaatgcaa gaaacactgc tttggcaaga ttgcaaggat tgggagattc attcagagct      420
```

```
tatcaacaaa gtttggaaga ttggttggaa aacagaaatg atgcaagaac aagaagtgtt      480
ctttacactc aatatattgc tttggaattg gatttcttga atgcaatgcc attatttgca      540
atcagagaac aagaagttcc tttgttgatg gtttatgctc aagctgcaaa tcttcatctt      600
cttcttttga gagatgcttc tctttatgga agagaatttg gacttacttc acaagaaatt      660
caaagatatt atgaaagaca agttgaaaga acaagagatt attctgatca ttgtgttcaa      720
tggtacaaca ctggattgaa caatttgaga ggaacaaatg ctgaaagttg ggtgagatac      780
aatcaattca gaagagattt gacacttgga gttttggatt tggttgcttt gtttccttca      840
tatgatacaa gaacatatcc aatcaacact tctgctcaat tgacaagaga gtttacact      900 gatgcaattg gagcaactgg agtgaacatg gcttcaatga attggtacaa caacaatgct      960
ccttcttttt ctgcaattga aactgctgtg atcagatctc tcatttgtt ggatttcttg     1020 gaacaattga agatttttc tgcttcttca agatggagca cacaagaca tatgacatat      1080 tggagaggac acacaattca atcaagacca attagaggag ctttgatcac ttcaactcat      1140
ggaaacacaa acacttcaat caatccagtg acatttcaat ttccttcaag atgtttac       1200 agaacagaaa gttatgctgg agttcttctt tggggaattt atttggaacc aattcatgga      1260
gttccaacag tgagattcaa tttcagaaat cctcaaaaca cttttgaaag aggaactgca      1320
aattattctc aaccatatga atctcctgga ttgcaattga agattcaga aacagaactt      1380 cctccagaaa aacagaaaag accaaattat gaaagctatt ctcacaggct ttctcacatt      1440
ggaatcattc ttcaaacaag attgaatgtt cctgtttatt catggacaca cagaagtgct      1500
gacagaacaa acacaattgg accaaacaga atcactcaaa ttcctgctgt gaaaggaaat      1560
cttctcttca atggaagtgt gatttctgga cctggattca ctggtggaga tttggtgaga      1620
ttgaacaatt ctggaaacaa cattcaaaac agaggatatt tggaagttcc aattcaattc      1680
acttcaactt caacaagata tagagtgaga gtgagatatg cttctgtgac accaattcat      1740
ctttctgtga attggggaaa ttcaaacatt ttttcttcaa cagttcctgc aactgctgct      1800
tctttggaca atcttcaatc aagagatttt ggatattttg aatcaacaaa tgctttcact      1860
tctgtcactg gaaatgttgt tggagtgaga aattttttcag aaaatgcaag agtgatcatt      1920
gacagatttg aatttattcc agtgacagca acatttgaag cagaa                      1965

<210> SEQ ID NO 13
<211> LENGTH: 1797
<212> TYPE: DNA
<213> ORGANISM: Artificial Sequence
<220> FEATURE:
<223> OTHER INFORMATION: synthethic nucleotide sequence encoding
      AXMI223z (axmi223zv03.03)

<400> SEQUENCE: 13
atgtcagaat atgaaaatgt tgaaccattt gtttctgttt caacaattca aactggaatt       60
ggaattgctg gaaaaattct tggaaatctt ggagttccat tgctggaca agttgcttct      120 ctttattctt tcattcttgg agaattgtgg ccaaaaggaa aatctcaatg ggaaattttc      180
atggaacatg ttgaagaatt gatcaatcaa aagatttcaa catatgcaag aaacaaagct      240
cttgctgatt tgaaaggatt gggagatgct cttgctgttt atcatgaaag tttggaaagt      300
tggatcaaga acagaaacaa cacaagaaca agaagtgttg tgaaaagcca atacatcact      360
ttggaattga tgtttgttca atctcttcct tcatttgctg tttctggaga agaagttcct      420
cttcttccaa tttatgctca agctgcaaat cttcatcttc ttcttctcag agatgcttca      480
```

| | |
|---|---|
| attttttggaa aagaatgggg attgagtgat tcagaaattt caacatttta caacagacaa | 540 |
| gttgaaagaa cttcagatta ttctgatcat tgcacaaaat ggtttgatac tggattgaac | 600 |
| agattgaaag gaagcaatgc tgaaatttgg gtgaaataca atcaattcag aagagatatg | 660 |
| acattgatgg ttttggattt ggttgctttg tttcaatcat atgatactca catgtatcca | 720 |
| atcaaaacaa ctgctcaatt gacaagagaa gtttacacaa atgcaattgg aactgttcat | 780 |
| cctcatcctt cttttgcttc aacaacttgg tacaacaaca atgctccttc tttttctgca | 840 |
| attgaagctg ctgtgatcag atctcctcat ttgttggatt tcttggaaca agtgacaatt | 900 |
| tattctcttc tttcaagatg gagcaacact caatatatga acatgtgggg aggacacaaa | 960 |
| cttgagttca gaacaattgg aggaacattg aacacttcaa ctcaaggatc aacaaacact | 1020 |
| tcaatcaatc cagtgacatt gccattcact tcaagagata tttacagaac agaatctctt | 1080 |
| gctggattga atttgttttt gacacaacca gtgaatggag ttccaagagt tgattttcat | 1140 |
| tggaaatttg tcactcatcc aattgcttca gacaattttt attatcctgg atatgctgga | 1200 |
| attggaactc aacttcaaga ttcagaaaat gaattgccac cagaaacaac tggacaacca | 1260 |
| aattatgaaa gctattctca caggcttttct cacattggat tgatttctgc ttctcatgtc | 1320 |
| aaaagcattgg tttattcttg gacacacaga agtgctgaca gaacaaacac aattcattca | 1380 |
| gattcaatca ctcaaattcc tttggtgaaa gctcacactc ttcaaagtgg aacaactgtt | 1440 |
| gtgaaaggac ctggattcac tggtggagat attttgagaa gaacaagtgg aggaccattt | 1500 |
| gcttttttcaa atgtgaattt ggattggaat cttttctcaaa gatatagagc aagaatcaga | 1560 |
| tatgcttcaa caacaatttt gagaatgtat gtgacaattg ctggagaaag aattttttgct | 1620 |
| ggacaattca acaaaacaat gaacactgga gatccattga catttcaaag tttttcatat | 1680 |
| gcaacaattg atactgcttt cacttttcca acaaaggctt cttcttttgac tgttggagct | 1740 |
| gatacatttt cttctggaaa tgaagtttat gttgacagat ttgaattgat tccagtt | 1797 |

<210> SEQ ID NO 14
<211> LENGTH: 1896
<212> TYPE: DNA
<213> ORGANISM: Artificial Sequence
<220> FEATURE:
<223> OTHER INFORMATION: synthethic nucleotide sequence encoding
      AXMI224z (axmi224zv03.03)

<400> SEQUENCE: 14

| | |
|---|---|
| atgaactctg ttttgaacag tggaagagca acaaatggag atgcttacaa tgttgttgct | 60 |
| catgatccat tttctttttca acacaaaagt ttggatacaa ttcaagaaga atggatggaa | 120 |
| tggaagaaag acaatcattc tctttatgtt gatccaattg ttggaactgt tgcttcttttt | 180 |
| cttctcaaga aagttggaag tttggttgga aaaaggattc tttcagaatt gagaaatttg | 240 |
| atttttcctt ctggttcaac aaatttgatg caagatattt tgagagaaac agaaaaattt | 300 |
| ttgaatcaaa gattgaacac tgatactttg gcaagagtga atgctgaatt gactggattg | 360 |
| caagcaaatg ttgaagagtt caacagacaa gttgacaatt tcttgaatcc aaacagaaat | 420 |
| gctgttcctc tttcaatcac ttcttctgtg aacacaatgc aacaattgtt tctcaacaga | 480 |
| ttgcctcaat ttcaaatgca aggatatcaa cttcttcttc ttcctttgtt tgctcaagct | 540 |
| gcaaatcttc atctttctttt catcagagat gtgattttga atgctgatga atggggaatt | 600 |
| tctgctgcaa cattgagaac atatcaaaat catttgagaa attacacaag agaatattca | 660 |
| aattattgca tcacaacata tcaaactgct ttcagaggat tgaacacaag attgcatgat | 720 |

| | |
|---|---|
| atgttggagt tcagaacata tatgttttg aatgttttg aatatgtttc aatttggagt | 780 |
| ttgttcaaat atcaaagttt gttggtttct tctggagcaa atctttatgc ttctggaagt | 840 |
| ggacctcaac aaactcaaag tttcacttct caagattggc catttcttta ttctttgttt | 900 |
| caagttaatt caaattatgt tttgaatgga ttttctggag caagattgac acaaacattt | 960 |
| ccaaacattg ttggattgcc aggaacaaca acaactcatg ctcttcttgc tgcaagagtt | 1020 |
| aattattctg gtgagtttc ttctggagat attggagctg ttttcaatca aaattttct | 1080 |
| tgttcaacat ttcttcctcc attgttgaca ccatttgtga aagttggtt ggattctgga | 1140 |
| agtgacagag gaggaatcaa cactgtgaca aattggcaaa cagaaagttt tgaaacaact | 1200 |
| cttggattga aagtggagc tttcactgca agaggaaatt caaattattt tccagattat | 1260 |
| ttcatcagaa acatttctgg agttcctttg gtggtgagaa atgaagattt gagaaggcct | 1320 |
| cttcattaca atcaaatcag aaacattgaa tcaccaagtg gaactcctgg aggattgaga | 1380 |
| gcttacatgg tttctgttca aacagaaaag aacaacattt atgctgttca tgaaaatgga | 1440 |
| acaatgattc atcttgctcc agaagattac actggattca caatttctcc aattcatgca | 1500 |
| actcaagtga acaatcaaac aagaactttc atttcagaaa aatttggaaa tcaaggagat | 1560 |
| tctttgagat ttgaacaaag caacacaaca gcaagatata ctttgagagg aaatggaaat | 1620 |
| tcttacaatc tttatttgag agtttcttca attggaaatt caacaatcag agtgacaatc | 1680 |
| aatggaagag tttacactgc ttcaaatgtc aacacaacaa caaacaatga tggagtgaat | 1740 |
| gacaatggag caagattttc tgatatcaac attggaaatg ttgttgcttc agacaacaca | 1800 |
| aatgttcctt tggacatcaa tgtgacattg aacagtggaa ctcaatttga attgatgaac | 1860 |
| atcatgtttg ttccaacaaa ttcttctcct ctttat | 1896 |

<210> SEQ ID NO 15
<211> LENGTH: 1821
<212> TYPE: DNA
<213> ORGANISM: Artificial Sequence
<220> FEATURE:
<223> OTHER INFORMATION: synthethic nucleotide sequence encoding
      AXMI225z (axmi225zv02.03)

<400> SEQUENCE: 15

| | |
|---|---|
| atggacaaca atccaaacat caatgaatgc attccttaca attgtttgtc aaatccagaa | 60 |
| gttgaagttc ttggaggaga aagaattgaa actggataca ctccaattga tatttctctt | 120 |
| tctttgacac aatttcttct ttcagaattt gttcctggtg ctggatttgt tcttggattg | 180 |
| gttgatatca tttggggaat tttggaccct ctcaatggg atgctttctt ggttcaaatt | 240 |
| gaacaattga tcaatcaaag aattgaagaa tttgcaagaa atcaagcaat ttcaagattg | 300 |
| gaaggattgt caaatcttta tcaaatttat gctgaaagtt tcagagcttg ggaagctgat | 360 |
| ccaacaaatc ctgctttgag agttgaaatg aggattcaat tcaatgatat gaactctgct | 420 |
| ttgacaacag caattccttt gtttgctgtt caaaattatc aagttcctct tctttcagtt | 480 |
| tatgttcaag ctgcaaatct tcatctttct gttttgagag atgtttctgt ttttggacaa | 540 |
| agatggggat tgatgcaac aacaatcaat tcaagataca atgatttgac aagattgatt | 600 |
| ggaaattaca ctgattatgc tgtgagatgg tacaacactg gattggaaag agtttgggga | 660 |
| ccagattcaa gagattggat cagatacaat caattcagaa gagaattgac attgacagtt | 720 |
| ttggatattg tttctttgtt tccaaattat gattcaagaa catatccaat cagaactgtt | 780 |
| tctcaattga caagagaaat ttacacaaat ccagtttgg aagatttcaa tggaagtttc | 840 |

```
agaggaagtg ctcaaggaat tgaacaaagc atcagatctc ctcatttgat ggatattctc      900
aattcaatca caatttacac tgatgctcac agaggatatt attattggag tggacatcaa      960
ataatggctt ctcctgttgg attttctgga cctgaattta catttcctct ttatggaaca     1020
atgggaaatg ctgctcctca acaaagaatt gttgctcaac ttggacaagg agtttacaga     1080
actctttctt caacatttta cagatctcct ttcaacattg gaatcaacaa tcaacaattg     1140
agtgttcttg atggaacaga atttgcttat ggaacttctt caaatcttcc ttctgctgtt     1200
tacagaaaaa gtggaactgt tgattctttg gatgaaattc ctcctcaaaa caacaatgtt     1260
cctccaagac aaggattttc tcacagattg agccatgttt caatgttcag aagtggattt     1320
tcaaattctt ctgtttcaat catcagagct ccaatgtttt cttggattca cagaagtgct     1380
gagttcaaca acatcattcc ttcttctcaa atcactcaaa ttccattgac aaaatcaaca     1440
aatcttggaa gtgaacttc tgttgtgaaa ggacctggat tcactggtgg tgatattttg     1500
agaagaactt ctcctggaca aatttcaaca ttgagagtga acatcactgc tcctctttct     1560
caaagataca gagtgagaat cagatatgct tcaacaacaa atcttcaatt tcacacttca     1620
attgatggaa ggccaatcaa tcaaggaaat ttttctgcaa caatgagttc tggaagcaat     1680
cttcaaagtg gaagtttcag aactgctgga ttcacaacac cattcaattt ttcaaatgga     1740
agttctgttt tcactctttc tgctcatgtt ttcaattctg gaatgaagt ttacattgac     1800 agaattgaat tgttcctgc t                                                1821

<210> SEQ ID NO 16
<211> LENGTH: 1986
<212> TYPE: DNA
<213> ORGANISM: Artificial Sequence
<220> FEATURE:
<223> OTHER INFORMATION: synthethic nucleotide sequence encoding
      AXMI221z (axmi221zv02.04)

<400> SEQUENCE: 16
atgaatcaaa acaaacatgg aatcattgga gcttcaaatt gtggatgcac ttcagacaat       60
gttgcaaaat atcctttggc aaacaatcct tattcttctg ctttgaattt gaactcttgc      120
caaaattctt caattttgaa ttggatcaac atcattggtg atgctgcaaa agaagctgtt      180
tcaattggaa caacaattgt ttctttgatc actgctcctt ctttgactgg tttgatttca      240
attgtttatg atttgattgg aaaagttctt ggaggaagtt ctggacaaag catttcagat      300 cttctcaattt gtgatttgct ttcaatcatt gatttgagag tgaatcaaag tgttttgaat      360
gatgaaattg ctgatttcaa tggaagtgtt ttgctttaca gaaattattt ggaagcattg      420
gattcttgga caaaaatcc aaattctgct tctgctgaag aattgagaac aagattcaga      480
attgctgatt cagaatttga cagaattttg acaagaggaa gtttgacaaa tggaggaagt      540
ttggcaaggc aaaatgctca aattcttctt cttccttctt ttgcttctgc tgctttcttt      600
catttgttgt tgttgagaga tgcaacaaga tatggaacaa attggggatt atacaatgca      660
actcctttca tcaattatca aagcaaattg gtggaattga ttgaacttta cactgattat      720
tgtgttcatt ggtacaacag aggattcaat gaattgaggc aaagaggaac ttcagcaact      780
gcttggttgg aatttcacag atacagaaga gaaatgacat tgatggtttt ggatattgtt      840
gcttcttttt cttctttgga tattacaaat tatccaattg aaacagattt tcaactttca      900
agagtgattt acactgatcc aattggattt gttcacagaa gttcttttgag aggagaaagc      960 tggttttctt ttgtgaacag agcaaatttt tcagatttgg aaaatgcaat tccaaatcca     1020
```

```
agaccaagtt ggttttgaa caacatgatc atttcaactg gaagtttgac attgcctgtt      1080
tctccaaaca ctgacagagc aagagtttgg tatggatcaa gagacagaat ttctccagca      1140
aattctcaag tgatttcaga attgattct ggacaacata caaattcaac tcaaacaatt       1200
cttggaagaa acattttcag aattgattct caagcatgca atttgaatga tacaacttat      1260
ggagtgaaca gagctgtttt ttatcatgat gcttcagaag aagccaaag aagtgtttat       1320 gaaggattca tcagaacaac tggaattgac aatccaagag ttcaaaacat caacacttat      1380
tttcctggag aaaattcaaa cattccaact ccagaagatt acactcattt gctttcaaca      1440
actgttaatt tgactggtgg attgagacaa gttgcaaaca acagaagaag ttcaattgtg      1500
atttatggat ggacacacaa aagtttgaca agaaacaaca ccatcaatcc tggaatcatc      1560
actcaaattc caatggtgaa actttcaaat cttccaagtg aacaaatgt tgttagagga       1620 cctggtttca ctggtggaga tattttgaga agaacaaatg ctggaaattt tggagatgtg      1680
agagtgaaca ttgctggaag tttgagccaa agatacagag tgagaatcag atatgcttca      1740
acaacaaatc ttcaatttca tacttcaatt aatggaagag caatcaatca agcaaatttt      1800
ccagcaacaa tgaacattgg agcttctttg aattacagaa cttcagaac tgttggattt        1860 acaactcctt tcacttttc agaagcaagt tcaattttca ctctttcaac tcattctttt        1920
tcttctggaa atgctgttta cattgacaga attgaatttg ttcctgctga gttactttt        1980 gaagct                                                                 1986

<210> SEQ ID NO 17
<211> LENGTH: 1965
<212> TYPE: DNA
<213> ORGANISM: Artificial Sequence
<220> FEATURE:
<223> OTHER INFORMATION: synthethic nucleotide sequence encoding
      AXMI222z (axmi222zv02.04)

<400> SEQUENCE: 17
atgaactcaa acagaaaaaa tgaaaatgaa atcattgatg cttcttcat tcctgctgtt        60 tcaaatgaaa gtgttacaat ttcaaaagaa tatgctcaaa caatcaact tcaaaacaat       120 tcaattgaag atggattatg cattgctgaa ggagaatata ttgatccttt tgtttctgct       180
tcaactgttc aaactggaat aagcattgct ggaagaattt tgggagttct ggagttcct        240 tttgctggac aacttgcttc attttattct tcattgttg agaactttg gccaaaagga        300 agagatcaat gggaaatttt catggaacat gttgaacaat tggtgaggca acaaatcact      360
gcaaatgcaa gaaacactgc tttggcaaga ttgcaaggat tgggagattc attcagagct      420
tatcaacaaa gtttggaaga ttggttggaa aacagaaatg atgcaagaac aagaagtgtt      480
ctttacactc aatatattgc tttggaattg gattttttga atgcaatgcc attatttgca      540
atcagagaac aagaagttcc tttgttgatg gtttatgctc aagctgcaaa tcttcatttg      600
ttgttgttga gatgcttc tctttatgga agagaatttg gtcttacttc tcaagaaatt        660
caaagatatt atgaaagaca agttgaaaga acaagagatt attcagatca ttgtgttcaa      720
tggtacaaca ctggtttgaa caatttgaga ggaacaaatg ctgaaagttg ggtgagatac      780
aatcaattca aagagatttt gacattggga gttttggatt tggttgcttt gtttccttct      840
tatgatacaa gaacttatcc aatcaacact tcagctcaat tgacaagaga agtttacact      900
gatgcaattg gagcaactgg agtgaacatg gcttcaatga attggtacaa caacaatgct      960
ccttcttttt cagcaattga aactgctgtg atcagatctc ctcattgtt ggattttttg        1020
```

-continued

```
gaacaattga agatttttc tgcttcttca agatggagca acacaagaca tatgacatat      1080
tggagaggac atacaattca atcaagacca attagaggag cttgatcac ttcaactcat      1140 ggaaatacaa acacttcaat caatcctgtt acttttcaat ttccttcaag agatgtttac    1200
agaacagaaa gctatgctgg agttcttctt tggggaattt atttggaacc aattcatgga    1260
gttccaacag tgagattcaa tttcagaaat cctcaaaaca cttttgaaag aggaactgca    1320
aattattctc aaccatatga atctcctggt ttgcaattga agattcaga acagagctt      1380 cctccagaaa caacagaaag accaaattat gaaagctatt ctcacaggct ttctcatatt    1440
ggaatcattc ttcaaacaag attgaatgtt cctgtttatt catggacaca cagaagtgct    1500
gacagaacaa atacaattgg accaaacaga atcactcaaa ttcctgctgt gaaaggaaat    1560
ttgcttttca atggaagtgt gatttctggt cctggtttca ctggtggaga tttggtgaga    1620
ttgaacaatt ctggaaacaa cattcaaaac agaggatatt tggaagttcc aattcaattc    1680
acttcaactt caacaagata tagagtgaga gtgagatatg cttctgttac tccaattcat    1740
ctttcagtga attggggaaa ttcaaacatt ttttcttcaa ctgttccagc aactgctgct    1800
tctttggaca atcttcaatc aagagatttt ggatattttg aatcaacaaa tgctttcact    1860
tctgttactg gaaatgttgt tggagtgaga aattttcag aaaatgcaag agtgatcatt      1920
gacagatttg aatttattcc tgttactgca acttttgaag ctgaa                    1965
```

<210> SEQ ID NO 18
<211> LENGTH: 1797
<212> TYPE: DNA
<213> ORGANISM: Artificial Sequence
<220> FEATURE:
<223> OTHER INFORMATION: synthethic nucleotide sequence encoding AXMI223z (axmi223zv03.04)

<400> SEQUENCE: 18

```
atgtcagaat atgaaaatgt tgaaccattt gtttctgttt caacaattca aactggaatt      60
ggaattgctg gaaaaattct tggaaatctt ggagttcctt ttgctggaca agttgcttct    120
ctttattctt tcattcttgg agaactttgg ccaaaaggaa aaagccaatg ggaaattttc    180
atggaacatg ttgaagaatt gatcaatcaa aagatttcaa cttatgcaag aaacaaagct    240
cttgctgatt tgaaaggatt gggagatgct ttggctgttt atcatgaaag tttggaaagt    300
tggatcaaaa acagaaacaa cacaagaaca agaagtgttg tgaaaagcca atacatcact    360
ttggaattga tgtttgttca agtttgcct tcatttgctg tttctggaga agaagttcct      420
ttgcttccaa tttatgctca agctgcaaat cttcatcttc ttcttctcag agatgcttca    480
attttgggaa agaatggggg attgagtgat tcagaaattt caacatttta caacagacaa    540
gttgaaagaa cttcagatta ttcagatcat tgcacaaaat ggtttgatac tggtttgaac    600
agattgaaag gaagcaatgc tgaaatttgg gtgaaataca atcaattcag aagagatatg    660
acattgatgg ttttggattt ggttgcttta tttcaaagct atgatactca tatgtatcca    720
atcaaaacaa ctgctcaatt gacaagagaa gtttatacaa atgcaattgg aactgttcat    780
cctcatcctt cttttgcttc aacaacatgg tacaacaaca atgctccttc tttttcagca    840
attgaagctg ctgtgatcag atctcctcat ttgttggatt ttttggaaca agttacaatt    900
tattctttgc tttcaagatg gagcaacact caatatatga acatgtgggg aggacacaaa    960
cttgagttca gaacaattgg aggaactttg aacacttcaa ctcaaggatc aacaaacact    1020
tcaatcaatc ctgttactct tccttcact tcaagagata tttacagaac agaaagtttg    1080
```

| | |
|---|---:|
| gctggtttga atttgttttt gacacaacca gtgaatggag ttccaagagt tgattttcat | 1140 |
| tggaaatttg ttactcatcc aattgcttca gacaattttt attatcctgg atatgctgga | 1200 |
| attggaactc aacttcaaga ttcagaaaat gaacttcctc cagaaacaac tggacaacca | 1260 |
| aattatgaaa gctattctca caggcttttct catattggat tgatttctgc ttctcatgtc | 1320 |
| aaagcattgg tttattcttg gacacacaga agtgctgaca gaacaaatac aattcattca | 1380 |
| gattcaatca ctcaaattcc tttggtgaaa gctcatactt tgcaaagtgg aacaactgtt | 1440 |
| gtgaaaggac ctggtttcac tggtggagat attttgagaa gaacaagtgg aggaccattt | 1500 |
| gcttttttcaa atgtgaattt ggattggaat ctttctcaaa gatatagagc aagaatcaga | 1560 |
| tatgcttcaa caacaaattt gagaatgtat gttacaattg ctggagaaag aattttttgct | 1620 |
| ggacaattca acaaaacaat gaacactgga gatccattga catttcaaag ttttttcttat | 1680 |
| gcaacaattg atactgcttt cacttttcca acaaaggctt cttcattgac tgttggagct | 1740 |
| gatacatttt cttctggaaa tgaagtttat gttgacagat ttgaattgat tccagtt | 1797 |

<210> SEQ ID NO 19
<211> LENGTH: 1896
<212> TYPE: DNA
<213> ORGANISM: Artificial Sequence
<220> FEATURE:
<223> OTHER INFORMATION: synthethic nucleotide sequence encoding
      AXMI224z (axmi224zv03.04)

<400> SEQUENCE: 19

| | |
|---|---:|
| atgaactctg ttttgaacag tggaagagca acaaatggag atgcttacaa tgttgttgct | 60 |
| catgatccat tttcttttca acacaaaagt ttggatacaa ttcaagaaga atggatggaa | 120 |
| tggaagaaag acaatcattc tctttatgtt gatccaattg ttggaactgt tgcttctttt | 180 |
| cttctcaaga aagttggaag tttggttgga aaaaggattc tttcagaatt gagaaatttg | 240 |
| atttttccaa gtggttcaac aaatttgatg caagatattt tgagagaaac agaaaaattt | 300 |
| ttgaatcaaa gattgaacac tgatactttg gcaagagtga atgctgaatt gactggtttg | 360 |
| caagcaaatg ttgaagagtt caacagacaa gttgacaatt ttttgaatcc aaacagaaat | 420 |
| gctgttcctc tttcaatcac ttcttcagtg aatacaatgc aacaactttt cttgaacaga | 480 |
| ttgcctcaat ttcaaatgca aggatatcaa cttcttcttc ttccctttgtt tgctcaagct | 540 |
| gcaaatcttc atctttcttt catcagagat gtgattttga atgctgatga atggggaatt | 600 |
| tctgctgcaa ctttgagaac ttatcaaaat catttgagaa attatacaag agaatattca | 660 |
| aattattgca ttacaactta tcaaactgct tcagaggat tgaatacaag attgcatgat | 720 |
| atgttggagt tcagaactta catgtttttg aatgttttg aatatgtttc aatttggagc | 780 |
| ttgttcaaat atcaaagttt gttggttcct tctggagcaa atctttatgc ttctggaagt | 840 |
| ggtcctcaac aaactcaaag tttcacttct caagattggc catttcttta ttctttgttt | 900 |
| caagttaatt caaattatgt tttgaatgga ttttctggag caagattgac acaaactttt | 960 |
| ccaaacattg ttggattgcc tggaacaaca acaactcatg ctttgcttgc tgcaagagtt | 1020 |
| aattattctg gtggagtttc ttctggagat attggagctg ttttcaatca aaatttttct | 1080 |
| tgttcaactt ttcttcctcc tttgttgaca ccatttgtga aagctggtt ggattctgga | 1140 |
| agtgacagag gaggaatcaa cactgttaca aattggcaaa cagaaagttt tgaaacaact | 1200 |
| ttgggattga gaagtggagc tttcactgca agaggaaatt caaattattt tccagattat | 1260 |
| ttcatcagaa acatttctgg agttcctttg gtggtgagaa atgaagattt gagaaggcca | 1320 |

| | |
|---|---|
| ttgcattaca atcaaatcag aaacattgaa tctccaagtg gaactcctgg tggattgaga | 1380 |
| gcttacatgg tttcagttca aacagaaaaa acaacatttt atgctgttca tgaaaatgga | 1440 |
| acaatgattc atcttgctcc agaagattac actggtttca ccatttctcc aattcatgca | 1500 |
| actcaagtga acaatcaaac aagaactttc atttcagaaa aatttggaaa tcaaggagat | 1560 |
| tctttgagat tgaacaaag caacacaact gcaagatata ctttgagagg aaatggaaat | 1620 |
| tcttacaatc tttatttgag agtttcttca attggaaatt caacaatcag agttacaatc | 1680 |
| aatggaagag tttacactgc ttcaaatgtc aacacaacaa caaacaatga tggagtgaat | 1740 |
| gacaatggag caagatttttc tgatatcaac attggaaatg ttgttgcttc agacaacaca | 1800 |
| aatgttcctt tggatatcaa tgttactttg aacagtggaa ctcaatttga attgatgaac | 1860 |
| atcatgtttg ttccaacaaa ttcttctcct ctttat | 1896 |

<210> SEQ ID NO 20
<211> LENGTH: 1821
<212> TYPE: DNA
<213> ORGANISM: Artificial Sequence
<220> FEATURE:
<223> OTHER INFORMATION: synthethic nucleotide sequence encoding
      AXMI225z (axmi225zv02.04)

<400> SEQUENCE: 20

| | |
|---|---|
| atggacaaca atccaaacat caatgaatgc attccttaca attgcttgtc aaatccagaa | 60 |
| gttgaagttc ttggaggaga agaattgaa actggatata ctccaattga tatttctctt | 120 |
| tctttgacac aatttcttct ttcagaattt gttcctggag ctggatttgt tcttggattg | 180 |
| gttgatatca tttggggaat ttttggtcct tctcaatggg atgctttttt ggttcaaatt | 240 |
| gaacaattga tcaatcaaag aattgaagaa tttgcaagaa atcaagcaat ttcaagattg | 300 |
| gaaggattgt caaatcttta tcaaatttat gctgaaagtt tcagagcttg ggaagctgat | 360 |
| ccaacaaatc cagcttttgag agttgaaatg aggattcaat tcaatgatat gaactcagct | 420 |
| ttgacaactg caattccttt gtttgctgtt caaaattatc aagttccttt gctttctgtt | 480 |
| tatgttcaag ctgcaaatct tcatctttct gttttgagag atgtttctgt ttttggacaa | 540 |
| agatggggat tgatgcaac aacaatcaat tcaagataca atgatttgac aagattgatt | 600 |
| ggaaattaca ctgattatgc tgtgagatgg tacaacactg gtttggaaag agtttgggga | 660 |
| ccagattcaa gagattggat cagatacaat caattcagaa gagaattgac attgactgtt | 720 |
| ttggatattg tttctttgtt tccaaattat gattcaagaa cttatccaat cagaactgtt | 780 |
| tctcaattga caagagaaat ttatacaaat cctgttttgg aagatttcaa tggaagtttc | 840 |
| agaggaagtg ctcaaggaat tgaacaaagc atcagatctc ctcatttgat ggatattttg | 900 |
| aactcaatta caatttacac tgatgctcac agaggatatt attattggag tggacatcaa | 960 |
| atcatggctt ctcctgttgg attttctgga ccagaattta cttttcctct ttatggaaca | 1020 |
| atgggaaatg ctgctcctca caaagaatt gttgctcaac ttggacaagg agtttataga | 1080 |
| actttgagtt caacatttta cagatctcct ttcaacattg gaatcaacaa tcaacaactt | 1140 |
| tctgtttttgg atggaacaga atttgcttat ggaacttctt caaatcttcc ttctgctgtt | 1200 |
| tacagaaaaa gtggaactgt tgattcttg gatgaaattc ctcctcaaaa caacaatgtt | 1260 |
| cctccaagac aaggattttc tcacagattg agccatgttt caatgttcag aagtggattt | 1320 |
| tcaaattctt ctgtttcaat catcagagct ccaatgtttt cttggattca cagaagtgct | 1380 |
| gagttcaaca acatcattcc ttcttctcaa atcactcaaa ttcctttgac aaaatcaaca | 1440 |

-continued

```
aatcttggaa gtggaacttc tgttgtgaaa ggacctggtt tcactggtgg tgatattttg    1500
agaagaactt ctcctggaca aatttcaact ttgagagtga acatcactgc tcctctttct    1560
caaagataca gagtgagaat cagatatgct tcaacaacaa atcttcaatt tcatacaagc    1620
attgatggaa ggccaatcaa tcaaggaaat ttttcagcaa caatgagttc tggaagcaat    1680
cttcaaagtg gaagtttcag aactgctggt ttcacaactc ctttcaattt ttcaaatgga    1740
agttctgttt tcactctttc tgctcatgtt tcaattctg gaaatgaagt ttacattgac     1800
agaattgaat ttgttccagc t                                              1821
```

<210> SEQ ID NO 21
<211> LENGTH: 1229
<212> TYPE: PRT
<213> ORGANISM: Bacillus thuringiensis

<400> SEQUENCE: 21

```
Met Asn Gln Asn Lys His Gly Ile Ile Gly Ala Ser Asn Cys Gly Cys
 1               5                  10                  15

Thr Ser Asp Asn Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Gly Gln
                85                  90                  95

Ser Ile Ser Asp Leu Ser Ile Cys Asp Leu Leu Ser Ile Ile Asp Leu
            100                 105                 110

Arg Val Asn Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe His Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300
```

-continued

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
            325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Asn Thr Asp Arg Ala Arg
            355                 360                 365

Val Trp Tyr Gly Ser Arg Asp Arg Ile Ser Pro Ala Asn Ser Gln Val
    370                 375                 380

Ile Ser Glu Leu Ile Ser Gly Gln His Thr Asn Ser Thr Gln Thr Ile
385                 390                 395                 400

Leu Gly Arg Asn Ile Phe Arg Ile Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Phe Ile Arg Thr Thr Gly
            435                 440                 445

Ile Asp Asn Pro Arg Val Gln Asn Ile Asn Thr Tyr Phe Pro Gly Glu
450                 455                 460

Asn Ser Asn Ile Pro Thr Pro Glu Asp Tyr Thr His Leu Leu Ser Thr
465                 470                 475                 480

Thr Val Asn Leu Thr Gly Gly Leu Arg Gln Val Ala Asn Asn Arg Arg
                485                 490                 495

Ser Ser Ile Val Ile Tyr Gly Trp Thr His Lys Ser Leu Thr Arg Asn
            500                 505                 510

Asn Thr Ile Asn Pro Gly Ile Ile Thr Gln Ile Pro Met Val Lys Leu
            515                 520                 525

Ser Asn Leu Pro Ser Gly Thr Asn Val Val Arg Gly Pro Gly Phe Thr
530                 535                 540

Gly Gly Asp Ile Leu Arg Arg Thr Asn Ala Gly Asn Phe Gly Asp Val
545                 550                 555                 560

Arg Val Asn Ile Ala Gly Ser Leu Ser Gln Arg Tyr Arg Val Arg Ile
                565                 570                 575

Arg Tyr Ala Ser Thr Thr Asn Leu Gln Phe His Thr Ser Ile Asn Gly
            580                 585                 590

Arg Ala Ile Asn Gln Ala Asn Phe Pro Ala Thr Met Asn Ile Gly Ala
            595                 600                 605

Ser Leu Asn Tyr Arg Thr Phe Arg Thr Val Gly Phe Thr Thr Pro Phe
610                 615                 620

Thr Phe Ser Glu Ala Ser Ser Ile Phe Thr Leu Ser Thr His Ser Phe
625                 630                 635                 640

Ser Ser Gly Asn Ala Val Tyr Ile Asp Arg Ile Glu Phe Val Pro Ala
                645                 650                 655

Glu Val Thr Phe Glu Ala Glu Ser Asp Leu Glu Arg Ala Gln Lys Ala
            660                 665                 670

Val Asn Ala Leu Phe Thr Ser Ser Asn Gln Ile Gly Leu Lys Thr Asp
            675                 680                 685

Val Thr Asp Tyr His Ile Asp Gln Val Ser Asn Leu Val Ala Cys Leu
            690                 695                 700

Ser Asp Glu Phe Cys Leu Asp Glu Lys Arg Glu Leu Ser Glu Lys Val
705                 710                 715                 720

Lys His Ala Lys Arg Leu Ser Asp Glu Arg Asn Leu Leu Gln Asp Pro

```
                    725                 730                 735
Asn Phe Arg Gly Ile Asn Arg Gln Leu Asp Arg Gly Trp Arg Gly Ser
                740                 745                 750

Thr Asp Ile Thr Ile Gln Gly Gly Asp Asp Val Phe Lys Glu Asn Tyr
                755                 760                 765

Val Thr Leu Pro Gly Thr Phe Asp Glu Cys Tyr Pro Thr Tyr Leu Tyr
                770                 775                 780

Gln Lys Ile Asp Glu Ser Lys Leu Lys Ala Tyr Thr Arg Tyr Glu Leu
785                 790                 795                 800

Arg Gly Tyr Ile Glu Asp Ser Gln Asp Leu Glu Val Tyr Leu Ile Arg
                805                 810                 815

Tyr Asn Ala Lys His Glu Thr Leu Asn Val Pro Gly Thr Gly Ser Leu
                820                 825                 830

Trp Pro Leu Ala Ala Glu Ser Ser Ile Gly Arg Cys Gly Glu Pro Asn
                835                 840                 845

Arg Cys Ala Pro His Ile Glu Trp Asn Pro Asp Leu Asp Cys Ser Cys
                850                 855                 860

Arg Asp Gly Glu Lys Cys Ala His His Ser His His Phe Ser Leu Asp
865                 870                 875                 880

Ile Asp Val Gly Cys Thr Asp Leu Asn Glu Asp Leu Gly Val Trp Val
                885                 890                 895

Ile Phe Lys Ile Lys Thr Gln Asp Gly His Ala Arg Leu Gly Asn Leu
                900                 905                 910

Glu Phe Leu Glu Glu Lys Pro Leu Leu Gly Glu Ala Leu Ala Arg Val
                915                 920                 925

Lys Arg Ala Glu Lys Lys Trp Arg Asp Lys Arg Asp Lys Leu Glu Leu
                930                 935                 940

Glu Thr Asn Ile Val Tyr Lys Glu Ala Lys Glu Ser Val Asp Ala Leu
945                 950                 955                 960

Phe Val Asp Ser Gln Tyr Asn Arg Leu Gln Thr Asp Thr Asn Ile Ala
                965                 970                 975

Met Ile His Ala Ala Asp Lys Arg Val His Arg Ile Arg Glu Ala Tyr
                980                 985                 990

Leu Pro Glu Leu Ser Val Ile Pro Gly Val Asn Ala Ala Ile Phe Glu
                995                1000                1005

Glu Leu Glu Gly Leu Ile Phe Thr Ala Phe Ser Leu Tyr Asp Ala Arg
                1010                1015                1020

Asn Val Ile Lys Asn Gly Asp Phe Asn His Gly Leu Ser Cys Trp Asn
1025                1030                1035                1040

Val Lys Gly His Val Asp Val Glu Glu Gln Asn Asn His Arg Ser Val
                1045                1050                1055

Leu Val Val Pro Glu Trp Glu Ala Glu Val Ser Gln Glu Val Arg Val
                1060                1065                1070

Cys Pro Gly Arg Gly Tyr Ile Leu Arg Val Thr Ala Tyr Lys Glu Gly
                1075                1080                1085

Tyr Gly Glu Gly Cys Val Thr Ile His Glu Ile Glu Asp His Thr Asp
                1090                1095                1100

Glu Leu Lys Phe Arg Asn Cys Glu Glu Glu Glu Gly Tyr Pro Asn Asn
1105                1110                1115                1120

Thr Val Thr Cys Asn Asp Tyr Thr Ala Asn Gln Asp Glu Tyr Lys Gly
                1125                1130                1135

Ala Tyr Pro Ser Arg Asn Gly Gly Tyr Glu Asp Thr Tyr Asp Thr Ser
                1140                1145                1150
```

Ala Ser Val His Tyr Asn Thr Pro Thr Tyr Glu Glu Ile Gly Thr
             1155                1160                1165

Asp Leu Gln Arg Tyr Asn Gln Cys Glu Asn Asn Arg Gly Tyr Gly Asn
1170                1175                1180

Tyr Thr Pro Leu Pro Ala Gly Tyr Val Thr Lys Glu Leu Glu Tyr Phe
1185                1190                1195                1200

Pro Glu Thr Asp Lys Val Trp Ile Glu Ile Gly Glu Thr Gly Thr
             1205                1210                1215

Phe Ile Val Asp Ser Val Glu Leu Leu Leu Met Glu Glu
             1220                1225

<210> SEQ ID NO 22
<211> LENGTH: 656
<212> TYPE: PRT
<213> ORGANISM: Bacillus thuringiensis

<400> SEQUENCE: 22

Met Asn Gln Asn Lys His Gly Ile Ile Gly Ala Ser Asn Cys Gly Cys
1               5                   10                  15

Thr Ser Asp Asn Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Asn Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe His Leu Leu Leu Leu Arg Asp Ala
    195                 200                 205

Thr Arg Tyr Gly Thr Asn Trp Gly Leu Tyr Asn Ala Thr Pro Phe Ile
210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr

```
            290                 295                 300
Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Asn Thr Asp Arg Ala Arg
        355                 360                 365

Val Trp Tyr Gly Ser Arg Asp Arg Ile Ser Pro Ala Asn Ser Gln Val
    370                 375                 380

Ile Ser Glu Leu Ile Ser Gly Gln His Thr Asn Ser Thr Gln Thr Ile
385                 390                 395                 400

Leu Gly Arg Asn Ile Phe Arg Ile Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Phe Ile Arg Thr Thr Gly
        435                 440                 445

Ile Asp Asn Pro Arg Val Gln Asn Ile Asn Thr Tyr Phe Pro Gly Glu
    450                 455                 460

Asn Ser Asn Ile Pro Thr Pro Glu Asp Tyr Thr His Leu Leu Ser Thr
465                 470                 475                 480

Thr Val Asn Leu Thr Gly Gly Leu Arg Gln Val Ala Asn Asn Arg Arg
                485                 490                 495

Ser Ser Ile Val Ile Tyr Gly Trp Thr His Lys Ser Leu Thr Arg Asn
            500                 505                 510

Asn Thr Ile Asn Pro Gly Ile Ile Thr Gln Ile Pro Met Val Lys Leu
        515                 520                 525

Ser Asn Leu Pro Ser Gly Thr Asn Val Val Arg Gly Pro Gly Phe Thr
    530                 535                 540

Gly Gly Asp Ile Leu Arg Arg Thr Asn Ala Gly Asn Phe Gly Asp Val
545                 550                 555                 560

Arg Val Asn Ile Ala Gly Ser Leu Ser Gln Arg Tyr Arg Val Arg Ile
                565                 570                 575

Arg Tyr Ala Ser Thr Thr Asn Leu Gln Phe His Thr Ser Ile Asn Gly
            580                 585                 590

Arg Ala Ile Asn Gln Ala Asn Phe Pro Ala Thr Met Asn Ile Gly Ala
        595                 600                 605

Ser Leu Asn Tyr Arg Thr Phe Arg Thr Val Gly Phe Thr Thr Pro Phe
    610                 615                 620

Thr Phe Ser Glu Ala Ser Ser Ile Phe Thr Leu Ser Thr His Ser Phe
625                 630                 635                 640

Ser Ser Gly Asn Ala Val Tyr Ile Asp Arg Ile Glu Phe Val Pro Ala
                645                 650                 655

<210> SEQ ID NO 23
<211> LENGTH: 662
<212> TYPE: PRT
<213> ORGANISM: Bacillus thuringiensis

<400> SEQUENCE: 23

Met Asn Gln Asn Lys His Gly Ile Ile Gly Ala Ser Asn Cys Gly Cys
1               5                   10                  15
```

-continued

```
Thr Ser Asp Asn Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Asn Gln Ser Val Leu Asn Asp Gly Ile Ala Asp Phe Asn Gly
            115                 120                 125

Ser Val Leu Leu Tyr Arg Asn Tyr Leu Glu Ala Leu Asp Ser Trp Asn
            130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe His Leu Leu Leu Leu Arg Asp Ala
        195                 200                 205

Thr Arg Tyr Gly Thr Asn Trp Gly Leu Tyr Asn Ala Thr Pro Phe Ile
        210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
            275                 280                 285

Thr Asn Tyr Pro Ile Glu Thr Asp Phe Gln Leu Ser Arg Val Ile Tyr
            290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Asn Thr Asp Arg Ala Arg
            355                 360                 365

Val Trp Tyr Gly Ser Arg Asp Arg Ile Ser Pro Ala Asn Ser Gln Val
            370                 375                 380

Ile Ser Glu Leu Ile Ser Gly Gln His Thr Asn Ser Thr Gln Thr Ile
385                 390                 395                 400

Leu Gly Arg Asn Ile Phe Arg Ile Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Phe Ile Arg Thr Thr Gly
```

```
                    435                 440                 445
Ile Asp Asn Pro Arg Val Gln Asn Ile Asn Thr Tyr Phe Pro Gly Glu
450                 455                 460

Asn Ser Asn Ile Pro Thr Pro Glu Asp Tyr Thr His Leu Leu Ser Thr
465                 470                 475                 480

Thr Val Asn Leu Thr Gly Gly Leu Arg Gln Val Ala Asn Asn Arg Arg
                    485                 490                 495

Ser Ser Ile Val Ile Tyr Gly Trp Thr His Lys Ser Leu Thr Arg Asn
                500                 505                 510

Asn Thr Ile Asn Pro Gly Ile Ile Thr Gln Ile Pro Met Val Lys Leu
        515                 520                 525

Ser Asn Leu Pro Ser Gly Thr Asn Val Val Arg Gly Pro Gly Phe Thr
    530                 535                 540

Gly Gly Asp Ile Leu Arg Arg Thr Asn Ala Gly Asn Phe Gly Asp Val
545                 550                 555                 560

Arg Val Asn Ile Ala Gly Ser Leu Ser Gln Arg Tyr Arg Val Arg Ile
                    565                 570                 575

Arg Tyr Ala Ser Thr Thr Asn Leu Gln Phe His Thr Ser Ile Asn Gly
                580                 585                 590

Arg Ala Ile Asn Gln Ala Asn Phe Pro Ala Thr Met Asn Ile Gly Ala
            595                 600                 605

Ser Leu Asn Tyr Arg Thr Phe Arg Thr Val Gly Phe Thr Thr Pro Phe
        610                 615                 620

Thr Phe Ser Glu Ala Ser Ser Ile Phe Thr Leu Ser Thr His Ser Phe
625                 630                 635                 640

Ser Ser Gly Asn Ala Val Tyr Ile Asp Arg Ile Glu Phe Val Pro Ala
                    645                 650                 655

Glu Val Thr Phe Glu Ala
            660

<210> SEQ ID NO 24
<211> LENGTH: 1237
<212> TYPE: PRT
<213> ORGANISM: Bacillus thuringiensis

<400> SEQUENCE: 24

Met Asn Ser Asn Arg Lys Asn Glu Asn Glu Ile Ile Asp Ala Ser Phe
1               5                   10                  15

Ile Pro Ala Val Ser Asn Glu Ser Val Thr Ile Ser Lys Glu Tyr Ala
                20                  25                  30

Gln Thr Asn Gln Leu Gln Asn Asn Ser Ile Glu Asp Gly Leu Cys Ile
            35                  40                  45

Ala Glu Gly Glu Tyr Ile Asp Pro Phe Val Ser Ala Ser Thr Val Gln
    50                  55                  60

Thr Gly Ile Ser Ile Ala Gly Arg Ile Leu Gly Val Leu Gly Val Pro
65                  70                  75                  80

Phe Ala Gly Gln Leu Ala Ser Phe Tyr Ser Phe Ile Val Gly Glu Leu
                85                  90                  95

Trp Pro Lys Gly Arg Asp Gln Trp Glu Ile Phe Met Glu His Val Glu
                100                 105                 110

Gln Leu Val Arg Gln Gln Ile Thr Ala Asn Ala Arg Asn Thr Ala Leu
            115                 120                 125

Ala Arg Leu Gln Gly Leu Gly Asp Ser Phe Arg Ala Tyr Gln Gln Ser
    130                 135                 140
```

```
Leu Glu Asp Trp Leu Glu Asn Arg Asn Asp Ala Arg Thr Arg Ser Val
145                 150                 155                 160

Leu Tyr Thr Gln Tyr Ile Ala Leu Glu Leu Asp Phe Leu Asn Ala Met
            165                 170                 175

Pro Leu Phe Ala Ile Arg Glu Gln Glu Val Pro Leu Leu Met Val Tyr
            180                 185                 190

Ala Gln Ala Ala Asn Leu His Leu Leu Leu Arg Asp Ala Ser Leu
        195                 200                 205

Tyr Gly Arg Glu Phe Gly Leu Thr Ser Gln Glu Ile Gln Arg Tyr Tyr
        210                 215                 220

Glu Arg Gln Val Glu Arg Thr Arg Asp Tyr Ser Asp His Cys Val Gln
225                 230                 235                 240

Trp Tyr Asn Thr Gly Leu Asn Asn Leu Arg Gly Thr Asn Ala Glu Ser
            245                 250                 255

Trp Val Arg Tyr Asn Gln Phe Arg Arg Asp Leu Thr Leu Gly Val Leu
            260                 265                 270

Asp Leu Val Ala Leu Phe Pro Ser Tyr Asp Thr Arg Thr Tyr Pro Ile
        275                 280                 285

Asn Thr Ser Ala Gln Leu Thr Arg Glu Val Tyr Thr Asp Ala Ile Gly
290                 295                 300

Ala Thr Gly Val Asn Met Ala Ser Met Asn Trp Tyr Asn Asn Asn Ala
305                 310                 315                 320

Pro Ser Phe Ser Ala Ile Glu Thr Ala Val Ile Arg Ser Pro His Leu
            325                 330                 335

Leu Asp Phe Leu Glu Gln Leu Lys Ile Phe Ser Ala Ser Ser Arg Trp
            340                 345                 350

Ser Asn Thr Arg His Met Thr Tyr Trp Arg Gly His Thr Ile Gln Ser
            355                 360                 365

Arg Pro Ile Arg Gly Ala Leu Ile Thr Ser Thr His Gly Asn Thr Asn
370                 375                 380

Thr Ser Ile Asn Pro Val Thr Phe Gln Phe Pro Ser Arg Asp Val Tyr
385                 390                 395                 400

Arg Thr Glu Ser Tyr Ala Gly Val Leu Leu Trp Gly Ile Tyr Leu Glu
            405                 410                 415

Pro Ile His Gly Val Pro Thr Val Arg Phe Asn Phe Arg Asn Pro Gln
            420                 425                 430

Asn Thr Phe Glu Arg Gly Thr Ala Asn Tyr Ser Gln Pro Tyr Glu Ser
            435                 440                 445

Pro Gly Leu Gln Leu Lys Asp Ser Glu Thr Glu Leu Pro Pro Glu Thr
            450                 455                 460

Thr Glu Arg Pro Asn Tyr Glu Ser Tyr Ser His Arg Leu Ser His Ile
465                 470                 475                 480

Gly Ile Ile Leu Gln Thr Arg Leu Asn Val Pro Val Tyr Ser Trp Thr
            485                 490                 495

His Arg Ser Ala Asp Arg Thr Asn Thr Ile Gly Pro Asn Arg Ile Thr
            500                 505                 510

Gln Ile Pro Ala Val Lys Gly Asn Leu Leu Phe Asn Gly Ser Val Ile
            515                 520                 525

Ser Gly Pro Gly Phe Thr Gly Gly Asp Leu Val Arg Leu Asn Asn Ser
            530                 535                 540

Gly Asn Asn Ile Gln Asn Arg Gly Tyr Leu Glu Val Pro Ile Gln Phe
545                 550                 555                 560

Thr Ser Thr Ser Thr Arg Tyr Arg Val Arg Val Arg Tyr Ala Ser Val
```

```
                565                 570                 575
Thr Pro Ile His Leu Ser Val Asn Trp Gly Asn Ser Asn Ile Phe Ser
            580                 585                 590
Ser Thr Val Pro Ala Thr Ala Ala Ser Leu Asp Asn Leu Gln Ser Arg
            595                 600                 605
Asp Phe Gly Tyr Phe Glu Ser Thr Asn Ala Phe Thr Ser Val Thr Gly
            610                 615                 620
Asn Val Val Gly Val Arg Asn Phe Ser Glu Asn Ala Arg Val Ile Ile
625                 630                 635                 640
Asp Arg Phe Glu Phe Ile Pro Val Thr Ala Thr Phe Glu Ala Glu Tyr
                645                 650                 655
Asp Leu Glu Arg Ala Gln Glu Ala Val Asn Ala Leu Phe Thr Asn Thr
            660                 665                 670
Asn Pro Arg Arg Leu Lys Thr Asp Val Thr Asp Tyr His Ile Asp Gln
            675                 680                 685
Val Ser Asn Leu Val Ala Cys Leu Ser Asp Glu Phe Cys Leu Asp Glu
            690                 695                 700
Lys Arg Glu Leu Leu Glu Lys Val Lys Tyr Ala Lys Arg Leu Ser Asp
705                 710                 715                 720
Glu Arg Asn Leu Leu Gln Asp Pro Asn Phe Thr Ser Ile Asn Lys Gln
                725                 730                 735
Pro Asp Phe Ile Ser Thr Asn Glu Gln Ser Asn Phe Thr Ser Ile His
            740                 745                 750
Glu Gln Ser Glu His Gly Trp Trp Gly Ser Glu Asn Ile Thr Ile Gln
            755                 760                 765
Glu Gly Asn Asp Val Phe Lys Glu Asn Tyr Val Thr Leu Pro Gly Thr
            770                 775                 780
Tyr Asn Glu Cys Tyr Pro Thr Tyr Leu Tyr Gln Lys Ile Gly Glu Ser
785                 790                 795                 800
Glu Leu Lys Ala Tyr Thr Arg Tyr Gln Leu Arg Gly Tyr Ile Glu Asp
                805                 810                 815
Ser Gln Asp Leu Glu Ile Tyr Leu Ile Arg Tyr Asn Ala Lys His Glu
            820                 825                 830
Thr Leu Asp Val Pro Gly Thr Glu Ser Val Trp Pro Leu Ser Val Glu
            835                 840                 845
Ser Pro Ile Arg Arg Cys Gly Glu Pro Asn Arg Cys Ala Pro His Phe
            850                 855                 860
Glu Trp Asn Pro Asp Leu Asp Cys Ser Cys Arg Asp Gly Glu Lys Cys
865                 870                 875                 880
Ala His His Ser His His Phe Ser Leu Asp Ile Asp Val Gly Cys Ile
                885                 890                 895
Asp Leu His Glu Asn Leu Gly Val Trp Val Phe Lys Ile Lys Thr
            900                 905                 910
Gln Glu Gly His Ala Arg Leu Gly Asn Leu Glu Phe Ile Glu Lys
            915                 920                 925
Pro Leu Leu Gly Glu Ala Leu Ser Arg Val Lys Arg Ala Glu Lys Lys
            930                 935                 940
Trp Arg Asp Lys Arg Glu Lys Leu Gln Leu Glu Thr Lys Arg Val Tyr
945                 950                 955                 960
Thr Glu Ala Lys Glu Ala Val Asp Ala Leu Phe Val Asp Ser Gln Tyr
                965                 970                 975
Asp Arg Leu Gln Ala Asp Thr Asn Ile Gly Met Ile His Ala Ala Asp
            980                 985                 990
```

Lys Leu Val His Arg Ile Arg Glu Ala Tyr Leu Ser Glu Leu Ser Val
        995                 1000                1005

Ile Pro Gly Val Asn Ala Glu Ile Phe Glu Glu Leu Glu Gly Arg Ile
        1010                1015                1020

Ile Thr Ala Ile Ser Leu Tyr Asp Ala Arg Asn Val Val Lys Asn Gly
1025                1030                1035                1040

Asp Phe Asn Asn Gly Leu Ala Cys Trp Asn Val Lys Gly His Val Asp
                1045                1050                1055

Val Gln Gln Ser His His Arg Ser Val Leu Val Ile Pro Glu Trp Glu
                1060                1065                1070

Ala Glu Val Ser Gln Ala Val Arg Val Cys Pro Gly Arg Gly Tyr Ile
                1075                1080                1085

Leu Arg Val Thr Ala Tyr Lys Glu Gly Tyr Gly Glu Gly Cys Val Thr
                1090                1095                1100

Ile His Glu Ile Glu Asn Asn Thr Asp Glu Leu Lys Phe Lys Asn Cys
1105                1110                1115                1120

Glu Glu Glu Glu Val Tyr Pro Thr Asp Thr Gly Thr Cys Asn Asp Tyr
                1125                1130                1135

Thr Ala His Gln Gly Thr Ala Ala Cys Asn Ser Arg Asn Ala Gly Tyr
                1140                1145                1150

Glu Asp Ala Tyr Glu Val Asp Thr Thr Ala Ser Val Asn Tyr Lys Pro
                1155                1160                1165

Thr Tyr Glu Glu Glu Thr Tyr Thr Asp Val Arg Arg Asp Asn His Cys
                1170                1175                1180

Glu Tyr Asp Arg Gly Tyr Val Asn Tyr Pro Pro Val Pro Ala Gly Tyr
1185                1190                1195                1200

Met Thr Lys Glu Leu Glu Tyr Phe Pro Glu Thr Asp Lys Val Trp Ile
                1205                1210                1215

Glu Ile Gly Glu Thr Glu Gly Lys Phe Ile Val Asp Ser Val Glu Leu
                1220                1225                1230

Leu Leu Met Glu Glu
        1235

<210> SEQ ID NO 25
<211> LENGTH: 648
<212> TYPE: PRT
<213> ORGANISM: Bacillus thuringiensis

<400> SEQUENCE: 25

Met Asn Ser Asn Arg Lys Asn Glu Asn Glu Ile Ile Asp Ala Ser Phe
1               5                   10                  15

Ile Pro Ala Val Ser Asn Glu Ser Val Thr Ile Ser Lys Glu Tyr Ala
                20                  25                  30

Gln Thr Asn Gln Leu Gln Asn Asn Ser Ile Glu Asp Gly Leu Cys Ile
        35                  40                  45

Ala Glu Gly Glu Tyr Ile Asp Pro Phe Val Ser Ala Ser Thr Val Gln
        50                  55                  60

Thr Gly Ile Ser Ile Ala Gly Arg Ile Leu Gly Val Leu Gly Val Pro
65                  70                  75                  80

Phe Ala Gly Gln Leu Ala Ser Phe Tyr Ser Phe Ile Val Gly Glu Leu
                85                  90                  95

Trp Pro Lys Gly Arg Asp Gln Trp Glu Ile Phe Met Glu His Val Glu
                100                 105                 110

Gln Leu Val Arg Gln Gln Ile Thr Ala Asn Ala Arg Asn Thr Ala Leu

-continued

```
            115                 120                 125
Ala Arg Leu Gln Gly Leu Gly Asp Ser Phe Arg Ala Tyr Gln Gln Ser
130                 135                 140
Leu Glu Asp Trp Leu Glu Asn Arg Asn Asp Ala Arg Thr Arg Ser Val
145                 150                 155                 160
Leu Tyr Thr Gln Tyr Ile Ala Leu Glu Leu Asp Phe Leu Asn Ala Met
                    165                 170                 175
Pro Leu Phe Ala Ile Arg Glu Gln Glu Val Pro Leu Leu Met Val Tyr
                180                 185                 190
Ala Gln Ala Ala Asn Leu His Leu Leu Leu Arg Asp Ala Ser Leu
            195                 200                 205
Tyr Gly Arg Glu Phe Gly Leu Thr Ser Gln Glu Ile Gln Arg Tyr Tyr
210                 215                 220
Glu Arg Gln Val Glu Arg Thr Arg Asp Tyr Ser Asp His Cys Val Gln
225                 230                 235                 240
Trp Tyr Asn Thr Gly Leu Asn Asn Leu Arg Gly Thr Asn Ala Glu Ser
                    245                 250                 255
Trp Val Arg Tyr Asn Gln Phe Arg Arg Asp Leu Thr Leu Gly Val Leu
                260                 265                 270
Asp Leu Val Ala Leu Phe Pro Ser Tyr Asp Thr Arg Thr Tyr Pro Ile
            275                 280                 285
Asn Thr Ser Ala Gln Leu Thr Arg Glu Val Tyr Thr Asp Ala Ile Gly
290                 295                 300
Ala Thr Gly Val Asn Met Ala Ser Met Asn Trp Tyr Asn Asn Asn Ala
305                 310                 315                 320
Pro Ser Phe Ser Ala Ile Glu Thr Ala Val Ile Arg Ser Pro His Leu
                    325                 330                 335
Leu Asp Phe Leu Glu Gln Leu Lys Ile Phe Ser Ala Ser Ser Arg Trp
                340                 345                 350
Ser Asn Thr Arg His Met Thr Tyr Trp Arg Gly His Thr Ile Gln Ser
            355                 360                 365
Arg Pro Ile Arg Gly Ala Leu Ile Thr Ser Thr His Gly Asn Thr Asn
370                 375                 380
Thr Ser Ile Asn Pro Val Thr Phe Gln Phe Pro Ser Arg Asp Val Tyr
385                 390                 395                 400
Arg Thr Glu Ser Tyr Ala Gly Val Leu Leu Trp Gly Ile Tyr Leu Glu
                    405                 410                 415
Pro Ile His Gly Val Pro Thr Val Arg Phe Asn Phe Arg Asn Pro Gln
                420                 425                 430
Asn Thr Phe Glu Arg Gly Thr Ala Asn Tyr Ser Gln Pro Tyr Glu Ser
            435                 440                 445
Pro Gly Leu Gln Leu Lys Asp Ser Glu Thr Glu Leu Pro Pro Glu Thr
450                 455                 460
Thr Glu Arg Pro Asn Tyr Glu Ser Tyr Ser His Arg Leu Ser His Ile
465                 470                 475                 480
Gly Ile Ile Leu Gln Thr Arg Leu Asn Val Pro Val Tyr Ser Trp Thr
                    485                 490                 495
His Arg Ser Ala Asp Arg Thr Asn Thr Ile Gly Pro Asn Arg Ile Thr
                500                 505                 510
Gln Ile Pro Ala Val Lys Gly Asn Leu Leu Phe Asn Gly Ser Val Ile
            515                 520                 525
Ser Gly Pro Gly Phe Thr Gly Gly Asp Leu Val Arg Leu Asn Asn Ser
530                 535                 540
```

```
Gly Asn Asn Ile Gln Asn Arg Gly Tyr Leu Glu Val Pro Ile Gln Phe
545                 550                 555                 560

Thr Ser Thr Ser Thr Arg Tyr Arg Val Arg Val Arg Tyr Ala Ser Val
            565                 570                 575

Thr Pro Ile His Leu Ser Val Asn Trp Gly Asn Ser Asn Ile Phe Ser
            580                 585                 590

Ser Thr Val Pro Ala Thr Ala Ala Ser Leu Asp Asn Leu Gln Ser Arg
        595                 600                 605

Asp Phe Gly Tyr Phe Glu Ser Thr Asn Ala Phe Thr Ser Val Thr Gly
    610                 615                 620

Asn Val Val Gly Val Arg Asn Phe Ser Glu Asn Ala Arg Val Ile Ile
625                 630                 635                 640

Asp Arg Phe Glu Phe Ile Pro Val
                645
```

<210> SEQ ID NO 26
<211> LENGTH: 655
<212> TYPE: PRT
<213> ORGANISM: Bacillus thuringiensis

<400> SEQUENCE: 26

```
Met Asn Ser Asn Arg Lys Asn Glu Asn Glu Ile Ile Asp Ala Ser Phe
1               5                   10                  15

Ile Pro Ala Val Ser Asn Glu Ser Val Thr Ile Ser Lys Glu Tyr Ala
            20                  25                  30

Gln Thr Asn Gln Leu Gln Asn Asn Ser Ile Glu Asp Gly Leu Cys Ile
        35                  40                  45

Ala Glu Gly Glu Tyr Ile Asp Pro Phe Val Ser Ala Ser Thr Val Gln
    50                  55                  60

Thr Gly Ile Ser Ile Ala Gly Arg Ile Leu Gly Val Leu Gly Val Pro
65                  70                  75                  80

Phe Ala Gly Gln Leu Ala Ser Phe Tyr Ser Phe Ile Val Gly Glu Leu
                85                  90                  95

Trp Pro Lys Gly Arg Asp Gln Trp Glu Ile Phe Met Glu His Val Glu
            100                 105                 110

Gln Leu Val Arg Gln Gln Ile Thr Ala Asn Ala Arg Asn Thr Ala Leu
        115                 120                 125

Ala Arg Leu Gln Gly Leu Gly Asp Ser Phe Arg Ala Tyr Gln Gln Ser
    130                 135                 140

Leu Glu Asp Trp Leu Glu Asn Arg Asn Asp Ala Arg Thr Arg Ser Val
145                 150                 155                 160

Leu Tyr Thr Gln Tyr Ile Ala Leu Glu Leu Asp Phe Leu Asn Ala Met
                165                 170                 175

Pro Leu Phe Ala Ile Arg Glu Gln Glu Val Pro Leu Leu Met Val Tyr
            180                 185                 190

Ala Gln Ala Ala Asn Leu His Leu Leu Leu Arg Asp Ala Ser Leu
        195                 200                 205

Tyr Gly Arg Glu Phe Gly Leu Thr Ser Gln Glu Ile Gln Arg Tyr Tyr
    210                 215                 220

Glu Arg Gln Val Glu Arg Thr Arg Asp Tyr Ser Asp His Cys Val Gln
225                 230                 235                 240

Trp Tyr Asn Thr Gly Leu Asn Asn Leu Arg Gly Thr Asn Ala Glu Ser
                245                 250                 255

Trp Val Arg Tyr Asn Gln Phe Arg Arg Asp Leu Thr Leu Gly Val Leu
```

```
                    260             265             270
Asp Leu Val Ala Leu Phe Pro Ser Tyr Asp Thr Arg Thr Tyr Pro Ile
                275             280             285

Asn Thr Ser Ala Gln Leu Thr Arg Glu Val Tyr Thr Asp Ala Ile Gly
            290             295             300

Ala Thr Gly Val Asn Met Ala Ser Met Asn Trp Tyr Asn Asn Asn Ala
305             310             315             320

Pro Ser Phe Ser Ala Ile Glu Thr Ala Val Ile Arg Ser Pro His Leu
                325             330             335

Leu Asp Phe Leu Glu Gln Leu Lys Ile Phe Ser Ala Ser Ser Arg Trp
            340             345             350

Ser Asn Thr Arg His Met Thr Tyr Trp Arg Gly His Thr Ile Gln Ser
            355             360             365

Arg Pro Ile Arg Gly Ala Leu Ile Thr Ser Thr His Gly Asn Thr Asn
            370             375             380

Thr Ser Ile Asn Pro Val Thr Phe Gln Phe Pro Ser Arg Asp Val Tyr
385             390             395             400

Arg Thr Glu Ser Tyr Ala Gly Val Leu Leu Trp Gly Ile Tyr Leu Glu
                405             410             415

Pro Ile His Gly Val Pro Thr Val Arg Phe Asn Phe Arg Asn Pro Gln
                420             425             430

Asn Thr Phe Glu Arg Gly Thr Ala Asn Tyr Ser Gln Pro Tyr Glu Ser
            435             440             445

Pro Gly Leu Gln Leu Lys Asp Ser Glu Thr Glu Leu Pro Pro Glu Thr
        450             455             460

Thr Glu Arg Pro Asn Tyr Glu Ser Tyr Ser His Arg Leu Ser His Ile
465             470             475             480

Gly Ile Ile Leu Gln Thr Arg Leu Asn Val Pro Val Tyr Ser Trp Thr
                485             490             495

His Arg Ser Ala Asp Arg Thr Asn Thr Ile Gly Pro Asn Arg Ile Thr
            500             505             510

Gln Ile Pro Ala Val Lys Gly Asn Leu Leu Phe Asn Gly Ser Val Ile
        515             520             525

Ser Gly Pro Gly Phe Thr Gly Asp Leu Val Arg Leu Asn Asn Ser
    530             535             540

Gly Asn Asn Ile Gln Asn Arg Gly Tyr Leu Glu Val Pro Ile Gln Phe
545             550             555             560

Thr Ser Thr Ser Thr Arg Tyr Arg Val Arg Val Arg Tyr Ala Ser Val
                565             570             575

Thr Pro Ile His Leu Ser Val Asn Trp Gly Asn Ser Asn Ile Phe Ser
            580             585             590

Ser Thr Val Pro Ala Thr Ala Ala Ser Leu Asp Asn Leu Gln Ser Arg
        595             600             605

Asp Phe Gly Tyr Phe Glu Ser Thr Asn Ala Phe Thr Ser Val Thr Gly
    610             615             620

Asn Val Val Gly Val Arg Asn Phe Ser Glu Asn Ala Arg Val Ile Ile
625             630             635             640

Asp Arg Phe Glu Phe Ile Pro Val Thr Ala Thr Phe Glu Ala Glu
                645             650             655

<210> SEQ ID NO 27
<211> LENGTH: 719
<212> TYPE: PRT
<213> ORGANISM: Bacillus thuringiensis
```

<400> SEQUENCE: 27

```
Met Lys Leu Lys Asn Gln Asp Lys His Gln Ser Phe Ser Ser Asn Ala
 1               5                  10                  15

Lys Val Asp Lys Ile Ser Thr Asp Ser Leu Lys Asn Glu Thr Asp Ile
             20                  25                  30

Glu Leu Gln Asn Ile Asn His Glu Asp Cys Leu Lys Met Ser Glu Tyr
         35                  40                  45

Glu Asn Val Glu Pro Phe Val Ser Val Ser Thr Ile Gln Thr Gly Ile
 50                  55                  60

Gly Ile Ala Gly Lys Ile Leu Gly Asn Leu Gly Val Pro Phe Ala Gly
 65                  70                  75                  80

Gln Val Ala Ser Leu Tyr Ser Phe Ile Leu Gly Glu Leu Trp Pro Lys
             85                  90                  95

Gly Lys Ser Gln Trp Glu Ile Phe Met Glu His Val Glu Glu Leu Ile
            100                 105                 110

Asn Gln Lys Ile Ser Thr Tyr Ala Arg Asn Lys Ala Leu Ala Asp Leu
        115                 120                 125

Lys Gly Leu Gly Asp Ala Leu Ala Val Tyr His Glu Ser Leu Glu Ser
130                 135                 140

Trp Ile Lys Asn Arg Asn Asn Thr Arg Thr Arg Ser Val Val Lys Ser
145                 150                 155                 160

Gln Tyr Ile Thr Leu Glu Leu Met Phe Val Gln Ser Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Arg Asp Ala Ser Ile Phe Gly Lys
        195                 200                 205

Glu Trp Gly Leu Ser Asp Ser Glu Ile Ser Thr Phe Tyr Asn Arg Gln
210                 215                 220

Val Glu Arg Thr Ser Asp Tyr Ser Asp His Cys Thr Lys Trp Phe Asp
225                 230                 235                 240

Thr Gly Leu Asn Arg Leu Lys Gly Ser Asn Ala Glu Ile Trp Val Lys
                245                 250                 255

Tyr Asn Gln Phe Arg Arg Asp Met Thr Leu Met Val Leu Asp Leu Val
            260                 265                 270

Ala Leu Phe Gln Ser Tyr Asp Thr His Met Tyr Pro Ile Lys Thr Thr
        275                 280                 285

Ala Gln Leu Thr Arg Glu Val Tyr Thr Asn Ala Ile Gly Thr Val His
290                 295                 300

Pro His Pro Ser Phe Ala Ser Thr Thr Trp Tyr Asn Asn Asn Ala Pro
305                 310                 315                 320

Ser Phe Ser Ala Ile Glu Ala Ala Val Ile Arg Ser Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
        355                 360                 365

Thr Ile Gly Gly Thr Leu Asn Thr Ser Thr Gln Gly Ser Thr Asn Thr
370                 375                 380

Ser Ile Asn Pro Val Thr Leu Pro Phe Thr Ser Arg Asp Ile Tyr Arg
385                 390                 395                 400

Thr Glu Ser Leu Ala Gly Leu Asn Leu Phe Leu Thr Gln Pro Val Asn
```

```
                    405                 410                 415
Gly Val Pro Arg Val Asp Phe His Trp Lys Phe Val Thr His Pro Ile
                420                 425                 430

Ala Ser Asp Asn Phe Tyr Tyr Pro Gly Tyr Ala Gly Ile Gly Thr Gln
                435                 440                 445

Leu Gln Asp Ser Glu Asn Glu Leu Pro Pro Glu Thr Thr Gly Gln Pro
            450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile His Ser Asp Ser Ile Thr Gln Ile Pro Leu
            500                 505                 510

Val Lys Ala His Thr Leu Gln Ser Gly Thr Thr Val Val Lys Gly Pro
        515                 520                 525

Gly Phe Thr Gly Gly Asp Ile Leu Arg Arg Thr Ser Gly Gly Pro Phe
    530                 535                 540

Ala Phe Ser Asn Val Asn Leu Asp Trp Asn Leu Ser Gln Arg Tyr Arg
545                 550                 555                 560

Ala Arg Ile Arg Tyr Ala Ser Thr Thr Asn Leu Arg Met Tyr Val Thr
                565                 570                 575

Ile Ala Gly Glu Arg Ile Phe Ala Gly Gln Phe Asn Lys Thr Met Asn
            580                 585                 590

Thr Gly Asp Pro Leu Thr Phe Gln Ser Phe Ser Tyr Ala Thr Ile Asp
        595                 600                 605

Thr Ala Phe Thr Phe Pro Thr Lys Ala Ser Ser Leu Thr Val Gly Ala
    610                 615                 620

Asp Thr Phe Ser Ser Gly Asn Glu Val Tyr Val Asp Arg Phe Glu Leu
625                 630                 635                 640

Ile Pro Val Thr Ala Thr Leu Glu Ala Val Thr Asp Leu Glu Arg Ala
                645                 650                 655

Gln Lys Ala Val His Glu Leu Phe Thr Ser Thr Asn Pro Gly Gly Leu
            660                 665                 670

Lys Thr Asp Val Lys Asp Tyr His Ile Asp Gln Val Ser Asn Leu Val
        675                 680                 685

Glu Ser Leu Ser Asp Glu Phe Tyr Leu Asp Glu Lys Arg Glu Leu Phe
    690                 695                 700

Glu Ile Val Lys Tyr Ala Lys Gln Leu His Ile Glu Pro Asn Met
705                 710                 715

<210> SEQ ID NO 28
<211> LENGTH: 599
<212> TYPE: PRT
<213> ORGANISM: Bacillus thuringiensis

<400> SEQUENCE: 28

Met Ser Glu Tyr Glu Asn Val Glu Pro Phe Val Ser Val Ser Thr Ile
1               5                   10                  15

Gln Thr Gly Ile Gly Ile Ala Gly Lys Ile Leu Gly Asn Leu Gly Val
                20                  25                  30

Pro Phe Ala Gly Gln Val Ala Ser Leu Tyr Ser Phe Ile Leu Gly Glu
            35                  40                  45

Leu Trp Pro Lys Gly Lys Ser Gln Trp Glu Ile Phe Met Glu His Val
        50                  55                  60
```

```
Glu Glu Leu Ile Asn Gln Lys Ile Ser Thr Tyr Ala Arg Asn Lys Ala
 65                  70                  75                  80

Leu Ala Asp Leu Lys Gly Leu Gly Asp Ala Leu Ala Val Tyr His Glu
                 85                  90                  95

Ser Leu Glu Ser Trp Ile Lys Asn Arg Asn Asn Thr Arg Thr Arg Ser
            100                 105                 110

Val Val Lys Ser Gln Tyr Ile Thr Leu Glu Leu Met Phe Val Gln Ser
        115                 120                 125

Leu Pro Ser Phe Ala Val Ser Gly Glu Glu Val Pro Leu Leu Pro Ile
    130                 135                 140

Tyr Ala Gln Ala Ala Asn Leu His Leu Leu Leu Arg Asp Ala Ser
145                 150                 155                 160

Ile Phe Gly Lys Glu Trp Gly Leu Ser Asp Ser Glu Ile Ser Thr Phe
                165                 170                 175

Tyr Asn Arg Gln Val Glu Arg Thr Ser Asp Tyr Ser Asp His Cys Thr
            180                 185                 190

Lys Trp Phe Asp Thr Gly Leu Asn Arg Leu Lys Gly Ser Asn Ala Glu
        195                 200                 205

Ile Trp Val Lys Tyr Asn Gln Phe Arg Arg Asp Met Thr Leu Met Val
    210                 215                 220

Leu Asp Leu Val Ala Leu Phe Gln Ser Tyr Asp Thr His Met Tyr Pro
225                 230                 235                 240

Ile Lys Thr Thr Ala Gln Leu Thr Arg Glu Val Tyr Thr Asn Ala Ile
                245                 250                 255

Gly Thr Val His Pro His Pro Ser Phe Ala Ser Thr Thr Trp Tyr Asn
            260                 265                 270

Asn Asn Ala Pro Ser Phe Ser Ala Ile Glu Ala Ala Val Ile Arg Ser
        275                 280                 285

Pro His Leu Leu Asp Phe Leu Glu Gln Val Thr Ile Tyr Ser Leu Leu
    290                 295                 300

Ser Arg Trp Ser Asn Thr Gln Tyr Met Asn Met Trp Gly Gly His Lys
305                 310                 315                 320

Leu Glu Phe Arg Thr Ile Gly Gly Thr Leu Asn Thr Ser Thr Gln Gly
                325                 330                 335

Ser Thr Asn Thr Ser Ile Asn Pro Val Thr Leu Pro Phe Thr Ser Arg
            340                 345                 350

Asp Ile Tyr Arg Thr Glu Ser Leu Ala Gly Leu Asn Leu Phe Leu Thr
        355                 360                 365

Gln Pro Val Asn Gly Val Pro Arg Val Asp Phe His Trp Lys Phe Val
    370                 375                 380

Thr His Pro Ile Ala Ser Asp Asn Phe Tyr Tyr Pro Gly Tyr Ala Gly
385                 390                 395                 400

Ile Gly Thr Gln Leu Gln Asp Ser Glu Asn Glu Leu Pro Pro Glu Thr
                405                 410                 415

Thr Gly Gln Pro Asn Tyr Glu Ser Tyr Ser His Arg Leu Ser His Ile
            420                 425                 430

Gly Leu Ile Ser Ala Ser His Val Lys Ala Leu Val Tyr Ser Trp Thr
        435                 440                 445

His Arg Ser Ala Asp Arg Thr Asn Thr Ile His Ser Asp Ser Ile Thr
    450                 455                 460

Gln Ile Pro Leu Val Lys Ala His Thr Leu Gln Ser Gly Thr Thr Val
465                 470                 475                 480

Val Lys Gly Pro Gly Phe Thr Gly Gly Asp Ile Leu Arg Arg Thr Ser
```

```
                        485                 490                 495
Gly Gly Pro Phe Ala Phe Ser Asn Val Asn Leu Asp Trp Asn Leu Ser
            500                 505                 510

Gln Arg Tyr Arg Ala Arg Ile Arg Tyr Ala Ser Thr Thr Asn Leu Arg
            515                 520                 525

Met Tyr Val Thr Ile Ala Gly Glu Arg Ile Phe Ala Gly Gln Phe Asn
            530                 535                 540

Lys Thr Met Asn Thr Gly Asp Pro Leu Thr Phe Gln Ser Phe Ser Tyr
545                 550                 555                 560

Ala Thr Ile Asp Thr Ala Phe Thr Phe Pro Thr Lys Ala Ser Ser Leu
                565                 570                 575

Thr Val Gly Ala Asp Thr Phe Ser Ser Gly Asn Glu Val Tyr Val Asp
            580                 585                 590

Arg Phe Glu Leu Ile Pro Val
            595

<210> SEQ ID NO 29
<211> LENGTH: 666
<212> TYPE: PRT
<213> ORGANISM: Bacillus thuringiensis

<400> SEQUENCE: 29

Met Val Val Asn Lys Tyr Phe Leu Lys Asn Ile Arg Tyr Tyr Gln Ala
1               5                   10                  15

Asn Leu Val Ser Leu Ile Leu Ile Tyr Asn Leu Ile Phe Lys Glu Glu
            20                  25                  30

Phe Tyr Met Asn Ser Val Leu Asn Ser Gly Arg Ala Thr Asn Gly Asp
        35                  40                  45

Ala Tyr Asn Val Val Ala His Asp Pro Phe Ser Phe Gln His Lys Ser
    50                  55                  60

Leu Asp Thr Ile Gln Glu Glu Trp Met Glu Trp Lys Lys Asp Asn His
65                  70                  75                  80

Ser Leu Tyr Val Asp Pro Ile Val Gly Thr Val Ala Ser Phe Leu Leu
                85                  90                  95

Lys Lys Val Gly Ser Leu Val Gly Lys Arg Ile Leu Ser Glu Leu Arg
            100                 105                 110

Asn Leu Ile Phe Pro Ser Gly Ser Thr Asn Leu Met Gln Asp Ile Leu
        115                 120                 125

Arg Glu Thr Glu Lys Phe Leu Asn Gln Arg Leu Asn Thr Asp Thr Leu
    130                 135                 140

Ala Arg Val Asn Ala Glu Leu Thr Gly Leu Gln Ala Asn Val Glu Glu
145                 150                 155                 160

Phe Asn Arg Gln Val Asp Asn Phe Leu Asn Pro Asn Arg Asn Ala Val
                165                 170                 175

Pro Leu Ser Ile Thr Ser Ser Val Asn Thr Met Gln Gln Leu Phe Leu
            180                 185                 190

Asn Arg Leu Pro Gln Phe Gln Met Gln Gly Tyr Gln Leu Leu Leu Leu
        195                 200                 205

Pro Leu Phe Ala Gln Ala Ala Asn Leu His Leu Ser Phe Ile Arg Asp
    210                 215                 220

Val Ile Leu Asn Ala Asp Glu Trp Gly Ile Ser Ala Ala Thr Leu Arg
225                 230                 235                 240

Thr Tyr Gln Asn His Leu Arg Asn Tyr Thr Arg Glu Tyr Ser Asn Tyr
                245                 250                 255
```

```
Cys Ile Thr Thr Tyr Gln Thr Ala Phe Arg Gly Leu Asn Thr Arg Leu
            260                 265                 270

His Asp Met Leu Glu Phe Arg Thr Tyr Met Phe Leu Asn Val Phe Glu
            275                 280                 285

Tyr Val Ser Ile Trp Ser Leu Phe Lys Tyr Gln Ser Leu Leu Val Ser
            290                 295                 300

Ser Gly Ala Asn Leu Tyr Ala Ser Gly Ser Gly Pro Gln Gln Thr Gln
305                 310                 315                 320

Ser Phe Thr Ser Gln Asp Trp Pro Phe Leu Tyr Ser Leu Phe Gln Val
                325                 330                 335

Asn Ser Asn Tyr Val Leu Asn Gly Phe Ser Gly Ala Arg Leu Thr Gln
                340                 345                 350

Thr Phe Pro Asn Ile Val Gly Leu Pro Gly Thr Thr Thr His Ala
                355                 360                 365

Leu Leu Ala Ala Arg Val Asn Tyr Ser Gly Gly Val Ser Ser Gly Asp
            370                 375                 380

Ile Gly Ala Val Phe Asn Gln Asn Phe Ser Cys Ser Thr Phe Leu Pro
385                 390                 395                 400

Pro Leu Leu Thr Pro Phe Val Arg Ser Trp Leu Asp Ser Gly Ser Asp
                405                 410                 415

Arg Gly Gly Ile Asn Thr Val Thr Asn Trp Gln Thr Glu Ser Phe Glu
                420                 425                 430

Thr Thr Leu Gly Leu Arg Ser Gly Ala Phe Thr Ala Arg Gly Asn Ser
            435                 440                 445

Asn Tyr Phe Pro Asp Tyr Phe Ile Arg Asn Ile Ser Gly Val Pro Leu
            450                 455                 460

Val Val Arg Asn Glu Asp Leu Arg Arg Pro Leu His Tyr Asn Gln Ile
465                 470                 475                 480

Arg Asn Ile Glu Ser Pro Ser Gly Thr Pro Gly Gly Leu Arg Ala Tyr
                485                 490                 495

Met Val Ser Val His Asn Arg Lys Asn Asn Ile Tyr Ala Val His Glu
            500                 505                 510

Asn Gly Thr Met Ile His Leu Ala Pro Glu Asp Tyr Thr Gly Phe Thr
            515                 520                 525

Ile Ser Pro Ile His Ala Thr Gln Val Asn Asn Gln Thr Arg Thr Phe
            530                 535                 540

Ile Ser Glu Lys Phe Gly Asn Gln Gly Asp Ser Leu Arg Phe Glu Gln
545                 550                 555                 560

Ser Asn Thr Thr Ala Arg Tyr Thr Leu Arg Gly Asn Gly Asn Ser Tyr
                565                 570                 575

Asn Leu Tyr Leu Arg Val Ser Ser Ile Gly Asn Ser Thr Ile Arg Val
                580                 585                 590

Thr Ile Asn Gly Arg Val Tyr Thr Ala Ser Asn Val Asn Thr Thr Thr
            595                 600                 605

Asn Asn Asp Gly Val Asn Asp Asn Gly Ala Arg Phe Ser Asp Ile Asn
            610                 615                 620

Ile Gly Asn Val Val Ala Ser Asp Asn Thr Asn Val Pro Leu Asp Ile
625                 630                 635                 640

Asn Val Thr Leu Asn Ser Gly Thr Gln Phe Glu Leu Met Asn Ile Met
                645                 650                 655

Phe Val Pro Thr Asn Ser Ser Pro Leu Tyr
            660                 665
```

```
<210> SEQ ID NO 30
<211> LENGTH: 631
<212> TYPE: PRT
<213> ORGANISM: Bacillus thuringiensis

<400> SEQUENCE: 30
```

| | | | | | | | | | | | | | | |
|---|---|---|---|---|---|---|---|---|---|---|---|---|---|---|
| Met | Asn | Ser | Val | Leu | Asn | Ser | Gly | Arg | Ala | Thr | Asn | Gly | Asp | Ala | Tyr |
| 1 | | | | 5 | | | | | 10 | | | | | 15 |

Asn Val Val Ala His Asp Pro Phe Ser Phe Gln His Lys Ser Leu Asp
                20                  25                  30

Thr Ile Gln Glu Glu Trp Met Glu Trp Lys Lys Asp Asn His Ser Leu
            35                  40                  45

Tyr Val Asp Pro Ile Val Gly Thr Val Ala Ser Phe Leu Leu Lys Lys
        50                  55                  60

Val Gly Ser Leu Val Gly Lys Arg Ile Leu Ser Glu Leu Arg Asn Leu
65                  70                  75                  80

Ile Phe Pro Ser Gly Ser Thr Asn Leu Met Gln Asp Ile Leu Arg Glu
                85                  90                  95

Thr Glu Lys Phe Leu Asn Gln Arg Leu Asn Thr Asp Thr Leu Ala Arg
            100                 105                 110

Val Asn Ala Glu Leu Thr Gly Leu Gln Ala Asn Val Glu Glu Phe Asn
        115                 120                 125

Arg Gln Val Asp Asn Phe Leu Asn Pro Asn Arg Asn Ala Val Pro Leu
130                 135                 140

Ser Ile Thr Ser Ser Val Asn Thr Met Gln Gln Leu Phe Leu Asn Arg
145                 150                 155                 160

Leu Pro Gln Phe Gln Met Gln Gly Tyr Gln Leu Leu Leu Leu Pro Leu
                165                 170                 175

Phe Ala Gln Ala Ala Asn Leu His Leu Ser Phe Ile Arg Asp Val Ile
            180                 185                 190

Leu Asn Ala Asp Glu Trp Gly Ile Ser Ala Ala Thr Leu Arg Thr Tyr
        195                 200                 205

Gln Asn His Leu Arg Asn Tyr Thr Arg Glu Tyr Ser Asn Tyr Cys Ile
210                 215                 220

Thr Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Leu Val Ser Ser Gly
            260                 265                 270

Ala Asn Leu Tyr Ala Ser Gly Ser Gly Pro Gln Gln Thr Gln Ser Phe
        275                 280                 285

Thr Ser Gln Asp Trp Pro Phe Leu Tyr Ser Leu Phe Gln Val Asn Ser
290                 295                 300

Asn Tyr Val Leu Asn Gly Phe Ser Gly Ala Arg Leu Thr Gln Thr Phe
305                 310                 315                 320

Pro Asn Ile Val Gly Leu Pro Gly Thr Thr Thr His Ala Leu Leu
                325                 330                 335

Ala Ala Arg Val Asn Tyr Ser Gly Gly Val Ser Ser Gly Asp Ile Gly
            340                 345                 350

Ala Val Phe Asn Gln Asn Phe Ser Cys Ser Thr Phe Leu Pro Pro Leu
        355                 360                 365

Leu Thr Pro Phe Val Arg Ser Trp Leu Asp Ser Gly Ser Asp Arg Gly
370                 375                 380

Gly Ile Asn Thr Val Thr Asn Trp Gln Thr Glu Ser Phe Glu Thr Thr
385 390 395 400

Leu Gly Leu Arg Ser Gly Ala Phe Thr Ala Arg Gly Asn Ser Asn Tyr
405 410 415

Phe Pro Asp Tyr Phe Ile Arg Asn Ile Ser Gly Val Pro Leu Val Val
420 425 430

Arg Asn Glu Asp Leu Arg Arg Pro Leu His Tyr Asn Gln Ile Arg Asn
435 440 445

Ile Glu Ser Pro Ser Gly Thr Pro Gly Gly Leu Arg Ala Tyr Met Val
450 455 460

Ser Val His Asn Arg Lys Asn Asn Ile Tyr Ala Val His Glu Asn Gly
465 470 475 480

Thr Met Ile His Leu Ala Pro Glu Asp Tyr Thr Gly Phe Thr Ile Ser
485 490 495

Pro Ile His Ala Thr Gln Val Asn Asn Gln Thr Arg Thr Phe Ile Ser
500 505 510

Glu Lys Phe Gly Asn Gln Gly Asp Ser Leu Arg Phe Glu Gln Ser Asn
515 520 525

Thr Thr Ala Arg Tyr Thr Leu Arg Gly Asn Gly Asn Ser Tyr Asn Leu
530 535 540

Tyr Leu Arg Val Ser Ser Ile Gly Asn Ser Thr Ile Arg Val Thr Ile
545 550 555 560

Asn Gly Arg Val Tyr Thr Ala Ser Asn Val Asn Thr Thr Thr Asn Asn
565 570 575

Asp Gly Val Asn Asp Asn Gly Ala Arg Phe Ser Asp Ile Asn Ile Gly
580 585 590

Asn Val Val Ala Ser Asp Asn Thr Asn Val Pro Leu Asp Ile Asn Val
595 600 605

Thr Leu Asn Ser Gly Thr Gln Phe Glu Leu Met Asn Ile Met Phe Val
610 615 620

Pro Thr Asn Ser Ser Pro Leu
625 630

<210> SEQ ID NO 31
<211> LENGTH: 1177
<212> TYPE: PRT
<213> ORGANISM: Bacillus thuringiensis

<400> SEQUENCE: 31

Met Asp Asn Asn Pro Asn Ile Asn Glu Cys Ile Pro Tyr Asn Cys Leu
1 5 10 15

Ser Asn Pro Glu Val Glu Val Leu Gly Gly Glu Arg Ile Glu Thr Gly
20 25 30

Tyr Thr Pro Ile Asp Ile Ser Leu Ser Leu Thr Gln Phe Leu Leu Ser
35 40 45

Glu Phe Val Pro Gly Ala Gly Phe Val Leu Gly Leu Val Asp Ile Ile
50 55 60

Trp Gly Ile Phe Gly Pro Ser Gln Trp Asp Ala Phe Leu Val Gln Ile
65 70 75 80

Glu Gln Leu Ile Asn Gln Arg Ile Glu Glu Phe Ala Arg Asn Gln Ala
85 90 95

Ile Ser Arg Leu Glu Gly Leu Ser Asn Leu Tyr Gln Ile Tyr Ala Glu
100 105 110

Ser Phe Arg Ala Trp Glu Ala Asp Pro Thr Asn Pro Ala Leu Arg Val
115 120 125

```
Glu Met Arg Ile Gln Phe Asn Asp Met Asn Ser Ala Leu Thr Thr Ala
    130                 135                 140
Ile Pro Leu Phe Ala Val Gln Asn Tyr Gln Val Pro Leu Leu Ser Val
145                 150                 155                 160
Tyr Val Gln Ala Ala Asn Leu His Leu Ser Val Leu Arg Asp Val Ser
                165                 170                 175
Val Phe Gly Gln Arg Trp Gly Phe Asp Ala Thr Thr Ile Asn Ser Arg
            180                 185                 190
Tyr Asn Asp Leu Thr Arg Leu Ile Gly Asn Tyr Thr Asp Tyr Ala Val
        195                 200                 205
Arg Trp Tyr Asn Thr Gly Leu Glu Arg Val Trp Gly Pro Asp Ser Arg
    210                 215                 220
Asp Trp Ile Arg Tyr Asn Gln Phe Arg Arg Glu Leu Thr Leu Thr Val
225                 230                 235                 240
Leu Asp Ile Val Ser Leu Phe Pro Asn Tyr Asp Ser Arg Thr Tyr Pro
                245                 250                 255
Ile Arg Thr Val Ser Gln Leu Thr Arg Glu Ile Tyr Thr Asn Pro Val
            260                 265                 270
Leu Glu Asp Phe Asn Gly Ser Phe Arg Gly Ser Ala Gln Gly Ile Glu
        275                 280                 285
Gln Ser Ile Arg Ser Pro His Leu Met Asp Ile Leu Asn Ser Ile Thr
    290                 295                 300
Ile Tyr Thr Asp Ala His Arg Gly Tyr Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
            340                 345                 350
Gln Leu Gly Gln Gly Val Tyr Arg Thr Leu Ser Ser Thr Phe Tyr Arg
        355                 360                 365
Ser Pro Phe Asn Ile Gly Ile Asn Asn Gln Gln Leu Ser Val Leu Asp
    370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
            420                 425                 430
Val Ser Met Phe Arg Ser Gly Phe Ser Asn Ser Ser Val Ser Ile Ile
        435                 440                 445
Arg Ala Pro Met Phe Ser Trp Ile His Arg Ser Ala Glu Phe Asn Asn
    450                 455                 460
Ile Ile Pro Ser Ser Gln Ile Thr Gln Ile Pro Leu Thr Lys Ser Thr
465                 470                 475                 480
Asn Leu Gly Ser Gly Thr Ser Val Val Lys Gly Pro Gly Phe Thr Gly
                485                 490                 495
Gly Asp Ile Leu Arg Arg Thr Ser Pro Gly Gln Ile Ser Thr Leu Arg
            500                 505                 510
Val Asn Ile Thr Ala Pro Leu Ser Gln Arg Tyr Arg Val Arg Ile Arg
        515                 520                 525
Tyr Ala Ser Thr Thr Asn Leu Gln Phe His Thr Ser Ile Asp Gly Arg
    530                 535                 540
```

```
Pro Ile Asn Gln Gly Asn Phe Ser Ala Thr Met Ser Ser Gly Ser Asn
545                 550                 555                 560

Leu Gln Ser Gly Ser Phe Arg Thr Ala Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Ala Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
            645                 650                 655

Asp Glu Phe Cys Leu Asp Glu Lys Gln Glu Leu Ser Glu Lys Val Lys
        660                 665                 670

His Ala Lys Arg Leu Ser Asp Glu Arg Asn Leu Leu Gln Asp Pro Asn
    675                 680                 685

Phe Arg Gly Ile Asn Arg Gln Leu Asp Arg Gly Trp Arg Gly Ser Thr
690                 695                 700

Asp Ile Thr Ile Gln Gly Gly Asp Asp Val Phe Lys Glu Asn Tyr Val
705                 710                 715                 720

Thr Leu Pro Gly Thr Phe Asp Glu Cys Tyr Pro Thr Tyr Leu Tyr Gln
            725                 730                 735

Lys Ile Asp Glu Ser Lys Leu Lys Ala Tyr Thr Arg Tyr Gln Leu Arg
        740                 745                 750

Gly Tyr Ile Glu Asp Ser Gln Asp Leu Glu Ile Tyr Leu Ile Arg Tyr
    755                 760                 765

Asn Ala Lys His Glu Thr Val Asn Val Pro Gly Thr Gly Ser Leu Trp
770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
            805                 810                 815

Asp Gly Glu Met Cys Ala His His Ser His His Phe Ser Leu Asp Ile
        820                 825                 830

Asp Val Gly Cys Thr Asp Leu Asn Glu Asp Leu Gly Val Trp Val Ile
    835                 840                 845

Phe Lys Ile Lys Thr Gln Asp Gly His Ala Arg Leu Gly Asn Leu Glu
850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
            885                 890                 895

Thr Asn Ile Val Tyr Lys Glu Ala Lys Glu Ser Val Asp Ala Leu Phe
        900                 905                 910

Val Asn Ser Gln Tyr Asp Gln Leu Gln Ala Asp Thr Asn Ile Ala Met
    915                 920                 925

Ile His Ala Ala Asp Lys Arg Val His Ser Ile Arg Glu Ala Tyr Leu
930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
```

```
                965                 970                 975
Val Ile Lys Asn Gly Asp Phe Asn Asn Gly Leu Ser Cys Trp Asn Val
            980                 985                 990

Lys Gly His Val Asp Val Glu Glu Gln Asn Asn His Arg Ser Val Leu
            995                1000                1005

Val Val Pro Glu Trp Glu Ala Glu Val Ser Gln Glu Val Arg Val Cys
           1010                1015                1020

Pro Gly Arg Gly Tyr Ile Leu Arg Val Thr Ala Tyr Lys Glu Gly Tyr
1025                1030                1035                1040

Gly Glu Gly Cys Val Thr Ile His Glu Ile Glu Asn Asn Thr Asp Glu
            1045                1050                1055

Leu Lys Phe Ser Asn Cys Val Glu Glu Ile Tyr Pro Asn Asn Thr
            1060                1065                1070

Val Thr Cys Asn Asp Tyr Thr Val Asn Gln Glu Glu Tyr Gly Gly Ala
            1075                1080                1085

Tyr Thr Ser Arg Asn Arg Gly Tyr Asn Glu Ala Pro Ser Val Pro Ala
            1090                1095                1100

Asp Tyr Ala Ser Val Tyr Glu Glu Lys Ser Tyr Thr Asp Gly Arg Arg
1105                1110                1115                1120

Glu Asn Pro Cys Glu Phe Asn Arg Gly Tyr Arg Asp Tyr Thr Pro Leu
            1125                1130                1135

Pro Val Gly Tyr Val Thr Lys Glu Leu Glu Tyr Phe Pro Glu Thr Asp
            1140                1145                1150

Lys Val Trp Ile Glu Ile Gly Glu Thr Glu Gly Thr Phe Ile Val Asp
            1155                1160                1165

Ser Val Glu Leu Leu Leu Met Glu Glu
            1170                1175

<210> SEQ ID NO 32
<211> LENGTH: 607
<212> TYPE: PRT
<213> ORGANISM: Bacillus thuringiensis

<400> SEQUENCE: 32

Met Asp Asn Asn Pro Asn Ile Asn Glu Cys Ile Pro Tyr Asn Cys Leu
1               5                  10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160
```

-continued

Tyr Val Gln Ala Ala Asn Leu His Leu Ser Val Leu Arg Asp Val Ser
            165                 170                 175

Val Phe Gly Gln Arg Trp Gly Phe Asp Ala Thr Thr Ile Asn Ser Arg
        180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
        210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
            245                 250                 255

Ile Arg Thr Val Ser Gln Leu Thr Arg Glu Ile Tyr Thr Asn Pro Val
        260                 265                 270

Leu Glu Asp Phe Asn Gly Ser Phe Arg Gly Ser Ala Gln Gly Ile Glu
            275                 280                 285

Gln Ser Ile Arg Ser Pro His Leu Met Asp Ile Leu Asn Ser Ile Thr
        290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
            325                 330                 335

Leu Tyr Gly Thr Met Gly Asn Ala Ala Pro Gln Gln Arg Ile Val Ala
        340                 345                 350

Gln Leu Gly Gln Gly Val Tyr Arg Thr Leu Ser Ser Thr Phe Tyr Arg
            355                 360                 365

Ser Pro Phe Asn Ile Gly Ile Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
            405                 410                 415

Asn Asn Asn Val Pro Pro Arg Gln Gly Phe Ser His Arg Leu Ser His
        420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
            485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
            530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Ala Gly Phe Thr Thr Pro Phe Asn
            565                 570                 575

Phe Ser Asn Gly Ser Ser Val Phe Thr Leu Ser Ala His Val Phe Asn

```
                    580                 585                 590
Ser Gly Asn Glu Val Tyr Ile Asp Arg Ile Glu Phe Val Pro Ala
            595                 600                 605

<210> SEQ ID NO 33
<211> LENGTH: 4
<212> TYPE: PRT
<213> ORGANISM: Artificial Sequence
<220> FEATURE:
<223> OTHER INFORMATION: endoplasmic reticulum targeting peptide

<400> SEQUENCE: 33

Lys Asp Glu Leu
 1
```